(12) United States Patent
Kasuga et al.

(10) Patent No.: US 6,316,689 B1
(45) Date of Patent: *Nov. 13, 2001

(54) 25-HYDROXYVITAMIN $D_3$ 24-HYDROYLASE TRANSGENIC RATS

(75) Inventors: Hisao Kasuga; Masami Isaka; Kunio Matsuoka, all of Osaka (JP)

(73) Assignee: Takeda Chemical Industries, Inc., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/423,011

(22) PCT Filed: Apr. 27, 1998

(86) PCT No.: PCT/JP98/01922

§ 371 Date: Oct. 27, 1999

§ 102(e) Date: Oct. 27, 1999

(87) PCT Pub. No.: WO98/48616

PCT Pub. Date: Nov. 5, 1998

(30) Foreign Application Priority Data

Apr. 30, 1997 (JP) .................................................. 9-112502

(51) Int. Cl.[7] .................................................. G01N 33/00
(52) U.S. Cl. ....................... 800/3; 800/3; 800/9; 800/14; 800/25; 424/9.2; 435/325; 435/353
(58) Field of Search ................................ 424/94.1, 9.2; 800/2, 3, 21, 9, 13, 14, 18, 25; 536/23.2; 435/320.1, 325, 353; 514/2

(56) References Cited

U.S. PATENT DOCUMENTS 5,625,125  4/1997  Bennett .................................... 800/2

FOREIGN PATENT DOCUMENTS

0528360A2  2/1993  (EP) .
WO 96/34091  10/1996  (WO) .

OTHER PUBLICATIONS

Houdebine, LM, 1994. J Biotechnology 34(3):269–87.*
Kappel CA, etal., 1992. Curr Opin Biotechnol 3(5):548–53.*
Hodgson CP, 1995. Exp Opin Ther Patents 5(5):459–68.*
Pakula AA, et al., 1989. Annu Rev Genet 23:289–310.*
Mullins LJ, et al., 1996. J Clin Invest 98(11):S37–40.*
N19962671 *Refractory Angitis Investigation and Study Group Report 1995*, (1996) pp. 71–78 —only abstract submitted.
Y. Ohyama et al., "Cloning and Expression of cDNA encoding. . . " *1991 Federation of European Biochemical Societies*, Jan. 1991, pp. 195–198.
D. Lewis et al., "Osteoporosis induced in mice by overproduction of interluekin 4" *Pro. Natl. Acad. Sci. USA* vol. 90, Dec. 1993, pp. 11618–11622.
G. Dressler et al., "Deregulation of Pax–2 expression in transgenic mice generates . . . " *Nature* vol. 362, Mar. 4, 1993, pp. 65–67.
D. Lowden et al., "Renal cysts in transgenic mice expressing transforming . . . " *J. Lab. Clin. Med.* vol. 124, No. 3, Sep. 1994, pp. 386–394.
J. Mullins et al., "Fulminant hypertension in transgenic rats harbouring the mouse . . . " *Nature* vol. 344, Apr. 5, 1990, pp. 541–544.
Ohyama et al., "Structural characterization of the gene encoding rat 25–Hydroxyvitamin $D_3$24–Hydroxylase" Biochemistry 1993, 32:76–82.

* cited by examiner

Primary Examiner—Deborah J. R. Clark
Assistant Examiner—David Nikodem
(74) Attorney, Agent, or Firm—Mark Chao; Elaine M. Ramesh

(57) ABSTRACT

The transgenic animal of this invention can be used as an animal model for renal disease, bone disease, joint disease, pulmonary disease, hyperlipidemia, arteriosclerosis, cardiac disease, diabetes, obesity, digestive organ disease, infectious disease, allergic disease, endocrine disease, dementia or cancer, or complications thereof; and provides a nonhuman transgenic mammal for the unraveling of the mechanisms of said diseases, explorations for the development of therapeutic modalities for the diseases, and the screening of candidate therapeutic drugs.

16 Claims, 9 Drawing Sheets

SEQUENCE LISTING

```
<160> NUMBER OF SEQ ID NOS: 6

<210> SEQ ID NO 1
<211> LENGTH: 21
<212> TYPE: DNA
<213> ORGANISM: Rat

<400> SEQUENCE: 1
aggctgtgct gctaatgtca a                                              21

<210> SEQ ID NO 2
<211> LENGTH: 21
<212> TYPE: DNA
<213> ORGANISM: Rat
```

-continued

```
<400> SEQUENCE: 2
aagagtgggg gtcagagttc g                                         21

<210> SEQ ID NO 3
<211> LENGTH: 24
<212> TYPE: DNA
<213> ORGANISM: Rat

<400> SEQUENCE: 3
tgaggacatt actgaccgct cctt                                      24

<210> SEQ ID NO 4
<211> LENGTH: 24
<212> TYPE: DNA
<213> ORGANISM: Rat

<400> SEQUENCE: 4
agttgctgtg tgggacttgt ctgt                                      24

<210> SEQ ID NO 5
<211> LENGTH: 21
<212> TYPE: DNA
<213> ORGANISM: Rat

<400> SEQUENCE: 5
ctgtcttctt tcaacctgga t                                         21

<210> SEQ ID NO 6
<211> LENGTH: 21
<212> TYPE: DNA
<213> ORGANISM: Rat

<400> SEQUENCE: 6
ttagagttct gtggggcatt c                                         21
```

25-HYDROXYVITAMIN $D_3$ 24-HYDROYLASE TRANSGENIC RATS

This application is the National stage of International Application No. PCT/JP98/01922, filed on Apr. 27, 1998.

TECHNICAL FIELD

This invention relates to 25-hydroxyvitamin $D_3$ 24-hydroxylase transgenic animals.

BACKGROUND ART

The transgenic animal carries a gene introduced to its own or progenitor's germ cell line in an early stage of development (usually, single cells).

Wagner et al. (1981, ProNAS, USA, 78, 50169 and Stewart et al. (1982, Science, 217, 1046) describe transgenic mice carrying the human globin gene. Constantini et al. (1981, Nature, 294, 92) and Lacy et al. (1983, Cell, 34, 343) describe transgenic mice carrying the rabbit globin gene. McKnight et al. (1983, Cell, 34, 335) describe mice carrying a foreign transferrin gene. Brinstar et al. (1983, Nature, 306, 332) describe mice carrying a functionally introduced immunoglobulin gene.

With regard to transgenic mice carrying a foreign gene related to diseases of bone, there is the following report. Lewis, D. B. et al. (1993, ProNAS, USA, 90, 11618) describe mice carrying the mouse lck-IL4 gene introduced and report that the osteocalcin level in those mice was significantly low, with the animals manifesting osteoporosis-like symptoms.

Meanwhile, as mice carrying a foreign gene related to diseases of the kidney, the following reports are available. Doi, T. et al. (1988, Am. J. Pathol., 131, 398) describe mice carrying the bovine growth hormone gene introduced and report that those mice showed diffuse mesangial hyalinization at week 7 of age and advanced glomerulosclerosis at week 30 or later, and subsequently died of uremia.

Dressler, G. R. et al. (1993, Nature, 362, 65) describe mice carrying the Pax-2 gene introduced and report that, in their kidneys, expression of the gene could be confirmed and nephrotic symptoms such as glomerular atrophy and proteinuria were observed. Lowden, D. A. et al. (1993, J. Lab. Clin. Med., 124, 386) describe mice carrying a foreign TGF-α gene introduced and report that expression of the gene in the kidneys could be confirmed and such symptoms as cyst formation and glomerular hypertrophy were observed.

However, there is not known a rat carrying any foreign gene introduced which can serve as a model of bone disease or kidney disease.

It is known that vitamin D exists in the natural kingdom as two native forms, $D_2$ and $D_3$, and that whereas $D_2$ has a double bond at the 22-position and a methyl group at the 24-position of its side chain and occurs in plants, $D_3$ occurs in animals. As the 7-hydrocholesterol (provitamin $D_3$) produced in the human skin is exposed to ultraviolet light from 290 to 320 nm, it undergoes photodegradation involving cleavage of the B ring at the 9, 10-position to give provitamin $D_3$. This, in turn, is isomerized at body temperature to give vitamin $D_3$. The structure of vitamin $D_3$ contains 3 double bonds, resulting from cleavage of the B ring, in every other positions. Vitamin $D_3$ is coupled to a vitamin D-binding protein and the couple is transported to the liver, where the 25-position of its side chain is hydroxylated by the enzyme 25-hydroxylase present in the liver cell mitochondria to give 25-hydroxyvitamin $D_3$. This substance is thence transported to the kidneys and, depending on the calcium metabolism regulating hormones in the bloodstream, such as PTH, and the blood calcium concentration, it is further hydroxylated at the 1α-, 23-, 24- and 26-positions in the proximal renal tubules to give 1α,25-dihydroxyvitamin $D_3$, 23,25-dihydroxyvitamin $D_3$, 24,25-dihydroxyvitamin $D_3$ and 26,25-dihydroxyvitamin $D_3$, respectively. Among them, the metabolite having high biological activity is 1α,25-dihydroxyvitamin $D_3$, which elevates blood calcium and phosphorus levels and discharges bone metabolizing functions; namely it assists in the expression of osteopontin and osteocalcin by osteoblasts, inhibits production of proteoglycan and, conversely, enhances production of cell membrane-derived phospholipids to thereby accelerate calcification of the osteoblasts. Regarding the function of 24,25-dihydroxyvitamin $D_3$, this substance is known to inhibit formation of osteoclasts, promote expression of the osteocalcin gene and further reportedly accelerate calcification in vitamin D-deficient rats but this action is dependent on the 25-hydroxyvitamin $D_3$ 24-hydroxylase (also called vitamin $D_3$ 24-hydroxylase or 1α,25-dihydroxyvitamin $D_3$-hydroxylase) which is present in the proximal renal tubules. Furthermore, recent studies have revealed that this enzyme hydroxylates not only the 24-position but also the 26-position.

Among important known disorders of vitamin D metabolism are vitamin D-dependent disease Type II, rickets, osteomalacia, and so forth. Those diseases manifest dysosteogenesis and deformity of bone resulting from a disorder of calcification, and the occurrence of this disorder prior to closure of the epiphyses leads to rickets, while occurrence of the disorder at later times leads to osteomalacia. Aside from the above diseases, there exist risks for renal diseases inclusive of renal insufficiency, secondary hyperparathyroidism and hypercalcemia occurring either as complications of said diseases or independently.

Ohyama et al. (1989, FEBS Lett., 255, 405) succeeded in the purification of vitamin $D_3$ 24-hydroxylase from rat kidney mitochondria extracted after administration of vitamin D. Subsequently Ohyama et al. (1991, FEBES Lett., 278, 195) isolated a cDNA by the screening of clones using an anti-vitamin $D_3$ 24-hydroxylase antibody. It is known that this vitamin $D_3$ 24-hydroxylase cDNA has a full length of 3.2 K bases and contains a reading frame (generally called open reading frame) of 1542 bp for the translation of 514 amino acids and produces a protein having a molecular weight of 59,000. It has been shown that as 35 amino acids are cleaved off from the N-terminus of the above protein, a mature protein consisting of 479 amino acid residues and having a molecular weight of about 55,000 is produced. Moreover, the finding that its 462nd amino acid cysteine is bound to the 5-position of heme indicates that this protein has characteristics similar to those of mitochondrial protein P-450, and an expression experiment in COS cells gave evidence of expression as a protein. Meanwhile, human vitamin $D_3$ 24-hydroxylase cDNA has been isolated by Chen et al. (1993, ProNAS, USA, 90, 4543), the murine counterpart by Itoh et al. (1995, Biochemica et Biophysica Acta, 1264, 26), and guinea pig counterpart by Ohyama et al. (1996, Journal of Japan Society of Bone Metabolism, 14, 112). It has been shown that the amino acid sequences of the above rat, human, mouse and guinea pig versions of the enzyme have about 80 to 95% homology.

The functions of the enzyme in vivo has also been analyzed, and Shinki et al. (1992, J. Biol. Chem., 267, 13757) demonstrated by Northern analysis that vitamin $D_3$ 24-hydroxylase is induced by 1α,25-dihydroxyvitamin $D_3$. It was also shown that the reaction of 1α,25- dihydroxyvitamin $D_3$ is faster and higher in degree in the small intestine than in the kidneys. Furthermore, in the analysis of the relative reactivity of 25-hydroxyvitamin $D_3$ and 1α,25-dihydroxyvitamin $D_3$, the difference in Km value suggested that 1α,25-dihydroxyvitamin $D_3$ is higher in the substrate specificity of vitamin $D_3$ 24-hydroxylase. Bechen, M. J. et al. (1996, Biochemistry, 35, 8465) investigated the metabolism of 25-hydroxyvitamin $D_3$ experimentally in *Spodoptera frugiperda* (Sf21) cells and suggested that the enzyme has 23-/24-bicatalytic activity. Furthermore, vitamin $D_3$ 25-hydroxylase has been isolated from rat liver mitochondria by Masumoto et al. (1988, J. Biol. Chem., 263, 14256) and some light has been cast on the pertinent gene function as well. However, neither isolation and purification nor cloning of vitamin $D_3$ 1α-hydroxylase gene has been successful to this day.

Expression of vitamin $D_3$ 24-hydroxylase gene is regulated by the coupling of the heterodimer consisting of the vitamin $D_3$ receptor (generally abbreviated as VDR)-1α,25-dihydroxyvitamin $D_3$ complex and the retinoid X receptor (generally abbreviated as RXR) to the vitamin $D_3$ response element (generally abbreviated as VDRE) $VDRE_1$ located in the -150 to -136 region of the 5'-upstream. This vitamin $D_3$ response element has a repetitive structure of a motif consisting of the 6 bases of AGGTCA with 3 base gaps (generally called tandem repeat) and its similarity to the thyroid hormone response element (generally abbreviated as TRE) and retinoic acid response element (generally abbreviated as RARE) has been pointed out. Furthermore, Kerry, D. M. et al. (1996, J. Biol. Chem., 271, 29715) suggested that among the three vitamin $D_3$ response elements existing in the 5'-upstream of this gene, VDRE-1 which is situated in the -150 to -136 region is more sensitive to 1α,25-dihydroxyvitamin $D_3$ than is VDRE-2 which is situated in the -249 to -232 region and that those two elements cooperates to enhance the activity and modulate the response to 1α,25-dihydroxyvitamin $D_3$.

The important genes under up regulation of expression by 1α,25-dihydroxyvitamin $D_3$ include alkaline phosphatase, aldolase subunit B, glyceraldehyde-3-phosphate dehydrogenase, heat shock protein-70, calbindin-$D_{28K}$ and $_{9K}$, osteocalcin, osteopontin, osteonectin, fibronectin, interleukin I-6, matrix-gla-protein, metallothionein, NADH-DH subunit III and IV, integrin αVβ3, transforming growth factor β, nerve growth factor, c-FMS, c-fos, c-Ki-ras, vitamin $D_3$ receptor, 25-hydroxyvitamin $D_3$ 24-hydroxylase, protein kinase C, prolactin, plasma membrane calcium pump, EGF receptor, tumor necrosis factor α, 1α,25-dihydroxyvitamin $D_3$ receptor, etc. The important genes under down regulation of expression include NADH-DH subunit I, calcitonin, collagen type I, γ-interferon, colony stimulating factor, c-myb, 25-hydroxyvitamin $D_3$ 1α-hydroxylase, fatty acid-binding proteins, interleukin II and III, CD-23, transferrin receptor, cytochrome B, ferredoxin, parathyroid hormone (generally abbreviated as PTH), prepro-PTH, PTH-related proteins, protein kinase inhibitors, etc. It is known that the vitamin $D_3$ 24-hydroxylase, osteocalcin and osteopontin regulatory regions respectively have vitamin $D_3$-response elements and that the expression of those proteins is regulated by 1α,25-dihydroxyvitamin $D_3$ but it remains to be known as yet whether all of the above-enumerated genes are under the regulation through the vitamin $D_3$-response elements.

As 1α,25-dihydroxyvitamin $D_3$ was administered to a rat with vitamin $D_3$ deficiency, vitamin $D_3$ 24-hydroxylase was induced but its concentration and reaction time varied between the kidney and the small intestine, with a higher reactivity being found in the small intestine. It was shown that concurrent administration of parathyroid hormone and 1α,25-hydroxylated vitamin $D_3$ inhibited the induction of vitamin $D_3$ 24-hydroxylase. It was also shown that, in the kidneys, this enzyme is expressed in the proximal tube. Roy et al. (1996, Endocrinology, 137, 2938) demonstrated that, in the small intestine, this 1α,25-dihydroxyvitamin $D_3$-induced enzyme is expressed in the saccular gland columnar epithelium and villi.

Regarding vitamin D, reactions due to gene activation (generally called the genomic action of vitamin D) and other reactions (generally called the non-genomic action of vitamin D) are known and have been suggested to be associated with different physiological activities. As to the non-genomic action of vitamin D, there are mentioned such phenomena as promotion of the intestinal uptake of calcium and induction of an increase in intracellular calcium in a matter of a few minutes.

The metabolites of vitamin D in human plasma vary with assay conditions but taking vitamin $D_3$ as an example, reportedly its normal range in plasma is 1 to 5 ng/ml with an elimination half-life of 1 day; in the case of 25-hydroxyvitamin $D_3$ its normal range is 10 to 40 ng/ml with an elimination half-life of 10 to 20 days; in the case of 24-hydroxyvitamin $D_3$ its normal range is 1 to 4 ng/ml with an elimination half-life of 14 to 21 days; and in the case of 1α,25-dihydroxyvitamin $D_3$ its normal range is 20 to 70 pg/ml with an elimination half-life of several hours. 25-Hydroxyvitamin $D_3$ is produced in the liver, and this substance is little subject to metabolic regulation but is dependent on vitamin D intake and photobiosynthesis and can, therefore, be a nutritional marker of vitamin D deficiency. On the other hand, 1α,25-dihydroxyvitamin $D_3$ is regulated by the blood calcium concentration and-parathyroid hormone level and metabolized in the kidneys so that it is maintained at a constant concentration. Low plasma levels of this substance are found in certain diseases such as vitamin D-dependent disease type II, rickets, osteomalacia, chronic renal insufficiency, hypoparathyroidism, hyperthyroidism and osteoporosis, while high plasma levels are found in such diseases as secondary parathyroidism and hypercalcemia and in pregnancy. Thus, it is known that this substance can be a diagnostic marker of those diseases.

Nutritionally speaking, the intake of foods or preparations containing vitamin $D_2$ and vitamin $D_3$ is effective in vitamin D deficiency but administration of an activated vitamin D preparation is needed in vitamin D-resistant rickets, osteomalacia, osteoporosis, renal dystrophy, psoriasis and antineoplastic drug-induced rickets.

The synthesis of activated vitamin D derivatives is going on with avidity and a large number of derivatives have been synthesized. In line with this development, advances have been made in the study of the biological activity in cells and clinical effects of those derivatives as well, with the result that various vitamin D preparations are being used as therapeutic drugs for said diseases and even a large number of candidate derivatives for such therapeutic drugs are already known. Particularly, as epitomized by the report of Bouillon et al. (1995, Endocrine Reviews, 16, 200), many structure-activity relation studies have also been undertaken. Studies on the biological actions in cells and clinical effects of those substances have also made a rapid progress and, as a result, many vitamin D preparations are being used in the therapy of the above-mentioned diseases and a large number of derivatives are now earmarked as candidate therapeutic drugs.

Among them, 24-fluorinated vitamin $D_3$ has been studied in particular detail and as it was elucidated that the biological activity of 24,24-difluoro-25-hydroxyvitamin $D_3$ is not different from that of 24,25-hydroxyvitamin $D_3$, the function of 1α,25-dihydroxyvitamin $D_3$ 24-hydroxylase has come to be explored in greater depth. Beckman et al. (1996, Biochemistry, 35, 8465) demonstrated the multi-catalytic activity of this enzyme in an in vitro metabolism experiment. Thus, 25-hydroxyvitamin $D_3$ was metabolized to 25-hydroxy-24-oxovitamin $D_3$, to 24-oxo-23,25-hydroxyvitamin $D_3$ and further to 23-hydroxy-24,25,26,27-tetranorvitamin $D_3$, indicating that the activity of this enzyme is not limited to that of 24-hydroxylation but is multi-catalytic.

DISCLOSURE OF THE INVENTION

Elucidation of the vitamin $D_3$ 24-hydroxylase gene, particularly the unraveling of vitamin $D_3$ metabolism and its effects in diseases of bone, is a therapeutically important subject of study for the treatment of bone diseases (e.g. primary and secondary osteoporosis, rickets, osteomalacia, hypocalcemia, etc.) and renal diseases (e.g. glomerulonephritis, IgA nephropathy, membraneous nephropathy, glomerulosclerosis, nephrosis, renal insufficiency, etc.). Furthermore, it is an important research undertaking to elucidate the process of pathogenesis of renal disease, bone disease, joint diseases, pulmonary disease, hyperlipidemia, arteriosclerosis, cardiac disease, diabetes, obesity, digestive organ disease, infectious disease, allergic disease, endocrine disease, dementia and cancer through the quantitation of improvement in those diseases.

The transgenic animal, according to one aspect of this invention, provides the optimum model for studies on the function of vitamin $D_3$ 24-hydroxylase, studies on vitamin $D_3$ metabolism, studies for the establishment of prophylactic and therapeutic modalities for diseases of bone, supply of cells high-expressing gene, ligand-binding study of the vitamin D receptor, and elucidation of the target gene regulating mechanisms of nuclear receptors inclusive of the vitamin D receptor. The transgenic animal according to this invention, in which the overexpression of vitamin $D_3$ 24-hydroxylase promotes the imbalance of vitamin $D_3$ metabolism chiefly in the kidneys and the inactivation or suppression of the activated vitamin $D_3$-regulating genes, serves as an animal model enabling quantitation of the disease state-improving efficacy in renal disease, bone disease, joint disease, pulmonary disease, hyperlipidemia, arteriosclerosis, cardiac disease, diabetes, obesity, digestive organ disease, infectious disease, allergic disease, endocrine disease, dementia or cancer to thereby shed light on the mechanisms of those diseases and their complications.

However, there was not known a transgenic animal (especially a transgenic rat) which could be a well-qualified model of bone disease or renal disease and, therefore, be serviceable for the above-mentioned purposes.

It was, therefore, thought that should one be successful to construct a transgenic animal which carries a DNA into which a foreign 25-hydroxyvitamin $D_3$ 24-hydroxylase gene or a mutant gene thereof is inserted, which can be used as such a disease model, it should be possible to elucidate the functions of the vitamin $D_3$ 24-hydroxylase gene, particularly in the aspect of vitamin $D_3$ metabolism and its implications in diseases of bone, and permit studies for establishment of the prophylactic and therapeutic modalities for bone diseases, supply of high-gene-expression cells, ligand-binding study of the vitamin D receptor, and even explorations into the target gene regulating mechanisms of the nuclear receptors represented by the vitamin D receptor.

Exploring in earnest for solutions to the above problems, the inventors of this invention succeeded for the first time in constructing a nonhuman transgenic mammal carrying a DNA harboring a foreign 25-hydroxyvitamin $D_3$ 24-hydroxylase gene and found to anybody's surprise that this transgenic mammal develops renal disease and that the overexpression of vitamin $D_3$ 24-hydroxylase promotes the imbalance of vitamin $D_3$ metabolism chiefly in the kidneys and, through the inactivation or suppression of the functions of the activated vitamin $D_3$-regulating genes, induces renal disease, bone disease, joint disease, pulmonary disease, hyperlipidemia, arteriosclerosis, cardiac disease, diabetes, obesity, digestive organ disease, infectious disease, allergic disease, endocrine disease, dementia or cancer, inclusive of their complications, and, therefore, enables an assay of the disease state-improving efficacy of therapeutic agents in renal disease, bone disease, joint disease, pulmonary disease, hyperlipidemia, arteriosclerosis, cardiac disease, diabetes, obesity, digestive organ disease, infectious disease, allergic disease, endocrine disease, dementia or cancer.

This invention, therefore, relates to:
(1) a nonhuman mammal or a portion thereof which carries a DNA into which a foreign 25-hydroxyvitamin $D_3$ 24-hydroxylase gene or a mutant gene thereof is inserted;
(2) a mammal or portion of the above (1), wherein the nonhuman mammal is a rabbit, a dog, a cat, a guinea pig, a hamster, a mouse or a rat.
(3) a mammal or portion of the above (1), wherein the nonhuman mammal is a rat;
(4) a vector containing a foreign 25-hydroxyvitamin $D_3$ 24-hydroxylase gene or a mutant gene thereof and capable of expressing said gene in a mammal;
(5) a method of screening for a substance to be used for preventing and/or treating a disease resulting from abnormality of vitamin $D_3$ metabolism, which comprises applying an investigational substance to a nonhuman mammal or a portion thereof which carries a DNA into which a foreign 25-hydroxyvitamin $D_3$ 24-hydroxylase gene or a mutant gene thereof is inserted and assaying the resultant disease state-improving efficacy of said investigational substance in the disease resulting from abnormality of vitamin $D_3$ metabolism;
(6) a screening method of the above (5), wherein the disease resulting from abnormality of vitamin $D_3$ metabolism is a renal disease, a bone disease, a joint disease, a pulmonary disease, hyperlipidemia, arteriosclerosis, a cardiac disease, diabetes, obesity, a digestive organ disease, an infectious disease, an allergic disease, an endocrine disease, dementia or a cancer;
(7) a screening method of the above (5), wherein the disease resulting from abnormality of vitamin $D_3$ metabolism is a renal disease or a bone disease;
(8) A pharmaceutical composition for preventing and/or treating a disease resulting from abnormality of vitamin $D_3$ metabolism which comprises a substance determined to have a disease state-improving efficacy in a disease resulting from abnormality of vitamin $D_3$ metabolism by the method of the above (5);
(9) a pharmaceutical composition of the above (8), wherein the disease resulting from abnormality of vitamin $D_3$ metabolism is a renal disease, a bone disease, a joint disease, a pulmonary disease, hyperlipidemia, arteriosclerosis, cardiac disease, diabetes, obesity, a digestive organ disease, an infectious disease, an allergic disease, an endocrine disease, dementia or a cancer;
(10) a pharmaceutical composition of the above (8), wherein the disease resulting from abnormality of vitamin $D_3$ metabolism is a renal disease or a bone disease;
(11) use of a nonhuman mammal or a portion thereof which carries a DNA into which a foreign 25-hydroxyvitamin $D_3$ 24-hydroxylase gene or a mutant gene thereof is inserted for screening for a substance to be used for preventing and/or treating a disease resulting from abnormality of vitamin $D_3$ metabolism;
(12) a method of constructing the rat or portion of the above (3) which comprises introducing a DNA, into which a foreign 25-hydroxyvitamin $D_3$ 24-hydroxylase gene or a mutant gene thereof is inserted, into a fertilized egg harvested by mating a female rat pretreated with about 20 to 50 IU/animal of follicle stimulating hormone and then with about 0 to 10 IU/animal of luteinizing hormone with a male rat and implanting said fertilized egg in a female rat.

BRIEF DESCRIPTION OF THE DRAWINGS

In FIG. 2, lane 1 represents the marker (λ/HindIII+φx174/HaeIII), lane 2 represents a negative control, lane 3 represents R12123-6(+), lane 4 represents R12121-7(+), lane 5 represents R10175-9(?), lane 6 represents R11293-5(+), and lane 7 represents R11293-9(+).

In FIG. 3, lane 1 represents the marker (MLV-24-hydroxylase/ClaI) and lane 2 represents R9121-7/ClaI.

BEST MODE FOR CARRYING OUT THE INVENTION

Figure 1:
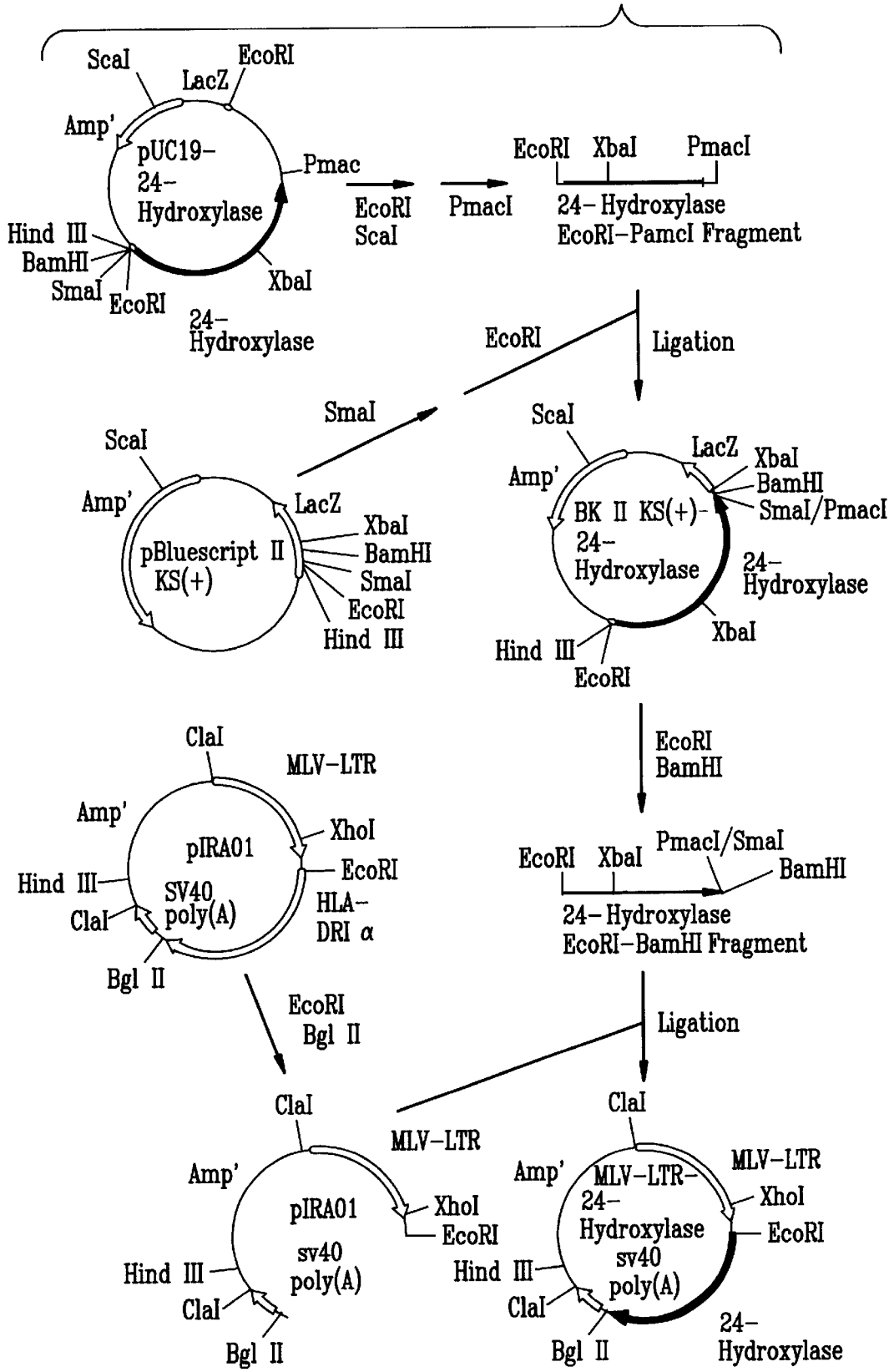
FIG. 1 is a schematic diagram showing the construction of plasmid pMLV-LTR-Vitamin $D_3$ 24-hydroxylase.

The transgenic animal of this invention can be produced by introducing a foreign 25-hydroxyvitamin $D_3$ 24-hydroxylase gene or a mutant gene thereof into target cells, for example, germ cells such as unfertilized egg cells, fertilized egg cells, sperm and its primordial cells, preferably during the period of embryogenesis in the development of a nonhuman mammal (more preferably in the single-cell or fertilized egg cell stage and generally up to the 8-cell stage embryo) by a gene introduce technique such as the calcium phosphate method, electric pulse method, lipofection method, aggregation method, microinjection method, particle gun method, DEAE-dextran method, and so forth. Moreover, by such a gene introduce technique, the gene can also be introduced into somatic cells or organ or tissue cells for culture of the cells or tissues. Moreover, by causing those cells to be fused to said germ cells by the per se known cell fusion technology, transgenic animals can be constructed.

Furthermore, portions of the transgenic animal thus constructed (for example, cells, tissues or organs which carry a DNA into which a foreign 25-hydroxyvitamin $D_3$ 24-hydroxylase gene or a mutant gene thereof is inserted, or cultures of cells or tissues derived therefrom and, where necessary, subcultures thereof) can also be used each as said "portion of a nonhuman mammal which carries a DNA into which a foreign 25-hydroxyvitamin $D_3$ 24-hydroxylase gene or a mutant gene thereof is inserted" according to this invention for the same purposes as said "nonhuman mammal which carries a DNA into which a foreign 25-hydroxyvitamin $D_3$ 24-hydroxylase gene or a mutant gene thereof is inserted" according to this invention.

The "nonhuman mammal" to which this invention can be applied includes bovine, pig, sheep, goat, rabbit, dog, cat, guinea pig, hamster, rat, mouse, and so forth. The preferred animal is the rabbit, dog, cat, guinea pig, hamster, mouse or rat. Particularly preferred, among them, are animals of the order Rodentia. In particular, rats (Wistar strain, SD strain, etc.), especially rats of Wistar strain, are the most preferred for the construction of disease models. Aside from the above animals, avian species such as chickens can also be used for the same purposes as said "nonhuman mammal" according to this invention.

The "mammal" to which this invention can be applied includes even humans as well as the "nonhuman mammal" enumerated above.

The foreign 25-hydroxyvitamin $D_3$ 24-hydroxylase gene to be introduced to the host nonhuman mammal includes but is not limited to the following.

The rat vitamin $D_3$ 24-hydroxylase was first isolated by Ohyama, et al. (1989, ProNAS, USA, 86, 8977). Being a protein having a molecular weight of about 55,000, this enzyme is a mitochondrial cytochrome P450 protein, and Ohyama et al. ultimately succeeded in isolating a 3.2 kbp complementary DNA (abbreviated as cDNA) by the assay using an anti-vitamin $D_3$ 24-hydroxylase antibody.

Regarding the structure and function of this gene, it is known that the amino terminal (generally abbreviated as N-terminal) 35-residue propeptide moiety is cleaved off after translation to give a mature 479-residue protein. In view of the fact that the cysteine 462 of this protein is coordinated to the 5th binding site of heme, it has also been shown that this protein has characteristics of P450 proteins. When the cDNA obtained is expressed in COS cells, vitamin $D_3$ 24-hydroxylase is produced, affirming that it is a cDNA of vitamin $D_3$ 24-hydroxylase in functional terms as well.

In addition to said rat vitamin $D_3$ 24-hydroxylase cDNA, the DNA sequences of human vitamin $D_3$ 24-hydroxylase cDNA (Chen et al., 1993, ProNAS, USA, 90, 4543), mouse vitamin $D_3$ 24-hydroxylase cDNA (Itoh et al., 1995, Biochemica et Biophysica Acta, 1264, 26), guinea pig vitamin $D_3$ 24-hydroxylase cDNA (Ohyama et al., 1996, J. of Japanese Society of Bone Metabolism, 14, 112), etc. are already known and the vitamin $D_3$ 24-hydroxylase cDNA of any animal species can be used as said foreign 25-hydroxyvitamin $D_3$ 24-hydroxylase gene to be introduced to the host nonhuman mammal.

The mutant gene of a foreign 25-hydroxyvitamin $D_3$ 24-hydroxylase gene, which can be used in this invention, includes the mutant genes derived by variation (e.g. mutation) of the native foreign 25-hydroxyvitamin $D_3$ 24-hydroxylase gene, specifically through base addition, deletion, or substitution, for instance. More particularly, the preferred mutation involves substitution, addition or deletion of 1 to 5 (preferably 1 or 2) amino acid residues in the amino acid sequence of the 25-hydroxyvitamin $D_3$ 24-hydroxylase as the result of said base addition, deletion or substitution and may be any kind of mutation provided that the function of the parent 25-hydroxyvitamin $D_3$ 24-hydroxylase will be preserved.

The foreign 25-hydroxyvitamin $D_3$ 24-hydroxylase gene or mutant gene thereof in this invention may be the gene derived from a mammal either hallogeneic or heterogeneic to the host nonhuman mammal to which the gene is to be introduced for expression. In introducing the gene to the host animal, it is generally preferable to use it in the form of a gene construct (e.g. a vector) which can be prepared by ligating the gene downstream of a promoter capable of causing expression of the gene in cells of the host animal. More particularly, when the human 25-hydroxyvitamin $D_3$ 24-hydroxylase gene is to be introduced, an objective nonhuman mammal capable of high expression of human 25-hydroxyvitamin $D_3$ 24-hydroxylase gene can be constructed by microinjecting a vector comprising said gene ligated downstream of a promoter capable of causing expression of human 25-hydroxyvitamin $D_3$ 24-hydroxylase gene as derived from a mammal carrying a 25-hydroxyvitamin $D_3$ 24-hydroxylase gene having high homology to human 25-hydroxyvitamin $D_3$ 24-hydroxylase gene (e.g. rabbit, dog, cat, guinea pig, hamster, rat, mouse, etc.; preferably rat) into fertilized eggs of the host nonhuman mammal (e.g. fertilized rat eggs).

As the 25-hydroxyvitamin $D_3$ 24-hydroxylase gene expression vector that can be used, there may be mentioned E. coli-derived plasmids, B. subtilis-derived plasmids, yeast-derived plasmids, bacteriophages such as λ phage, animal viruses such as retroviruses, e.g. Moloney leukemia virus, vaccinia viruses and vaculoviruses. Among them, E. coli-derived plasmids, B. subtilis-derived plasmids and yeast-derived plasmids are preferred, and E. coli-derived plasmids are particularly preferred.

As the promoter for regulating the expression of the 25-hydroxyvitamin $D_3$ 24-hydroxylase gene, there can be used the gene promoters derived from viruses (cytomegalovirus, Moloney leukemia virus, JC virus, papilloma virus, etc.) and gene promoters derived from various mammals (human, rabbit, dog, cat, guinea pig, hamster, rat, mouse, etc.) and avian species (chicken etc.) (e.g. albumin, endothelin, osteocalcin, muscle creatine kinase, collagen type I and type II, cyclic AMP-dependent protein kinase βI subunit, atrial natriuretic factor, dopamine β-hydroxylase, neurofilament light-chain, metallothionein I and IIA, tissue-inhibitor of metalloprotease 1, smooth muscle α-actin, polypeptide chain elongation factor 1α(EF-1α), β-actin, α- and β-myosin heavy-chains, myosin light-chains 1 and 2, myelin basic protein, serum amyloid P component, renin, etc.). Preferably, Moloney leukemia virus promoter and human and chick β-actin promoters, which insure systemically high expressions can be used. For bone-specific expressions in humans, rats or mice, promoters of the osteocalcin gene and estrogen receptor gene which are known to be expressed in bone are effective.

The above vector preferably contains a sequence which terminates the transcription of the objective messenger RNA (poly A, generally called terminator) in the transgenic mammal, and the gene expression can be manipulated using the sequence of the gene derived from a virus, a mammal or an avian species. Preferably, SV40 terminator from simian virus can be employed. Further, for a still higher expression of the target gene, the splicing signal, enhancer region and part of the eucaryotic intron of the gene can be ligated upstream of the 5'-end of the promoter region, between the promoter region and the translation region or downstream of the 3'-end of the translation region depending on the objective.

The translation region for vitamin $D_3$ 24-hydroxylase can be acquired by using the whole or a part of the DNA derived from the liver, kidney, fibroblast or other cells of various mammals (rabbit, dog, cat, guinea pig, hamster, rat, mouse, etc.) or the whole or a part of the genomic DNA derived from various commercial genomic DNA libraries as the starting material or by using the complementary DNA prepared from the RNA derived from the liver, kidney, or fibroblast cells by the known procedure as the starting material. As the foreign 25-hydroxyvitamin $D_3$ 24-hydroxylase gene, the complementary DNA prepared from the RNA of a patient's fibroblast cells by the known procedure can also be used as the starting material. Furthermore, using the translation region of a vitamin $D_3$ 24-hydroxylase obtained from said cells or tissues, a mutated translation region can also be constructed by, for example, the point mutation technique. Any of those materials can be utilized for the production of transgenic animals.

Any of the above translation regions can be ligated, in the form of a gene construct (e.g. vector) which can be expressed in a host animal, by the conventional genetic engineering technique comprising ligating it downstream of said promoter (preferably upstream of the transcription termination site) to provide a DNA into which the 25-hydroxyvitamin $D_3$ 24-hydroxylase gene is inserted.

Introduction of the 25-hydroxyvitamin $D_3$ 24-hydroxylase gene in the stage of fertilized egg cells insures that the gene is distributed in all the germ cells and somatic cells of the host mammal. The existence of the 25-hydroxyvitamin $D_3$ 24-hdyroxylase gene in the germ cells of the transgenic animal means that the 25-hydroxyvitamin $D_3$ 24-hydroxylase gene will exist in all the germ cells and somatic cells of the entire progeny of the transgenic animal. The offspring of such animals to which the gene is passed on will contain the 25-hydroxyvitamin $D_3$ 24-hydroxylase gene in all of their germ cells and somatic cells.

By acquiring homozygotes carrying the introduced gene in both of the homologous chromosomes, mating male and female individuals and verifying that all the progeny maintain the gene stably and harbor the same gene in excess, the animals can be bred from generation to generation in the usual breeding environment.

The fertilized egg for use in the introduction of a foreign 25-hydroxyvitamin $D_3$ 24-hydroxylase gene, a gene (preferably a gene not having an intron) different from the endogenous gene of a host nonhuman mammal, into the fertilized egg of the host animal (preferably a rat, more preferably a Wistar rat) or its progenitor can be obtained by mating a male nonhuman mammal (preferably a male rat, more preferably a male Wistar rat) with a female nonhuman mammal (preferably a female rat, more preferably a female Wistar rat) of the same strain.

The fertilized egg can be obtained from natural crossing but is preferably obtained by a method which comprises adjusting the sexual cycle of a female nonhuman mammal (preferably a female rat, more preferably a female Wistar rat) artificially and mating it with a male nonhuman mammal (preferably a male rat, more preferably a male Wistar rat). The preferred method for artificially modifying the sexual cycle of a female nonhuman mammal comprises giving a follicle stimulating hormone (pregnant mare's serum gonadotropin, generally abbreviated as PMSG) and then a luteinizing hormone (human chorionic gonadotropin, generally abbreviated as hCG), for example by intraperitoneal injection. The preferred hormone dosage and dosing interval vary with different kinds of nonhuman mammals. When a Wistar rat is used, preferred is a 8 week-old animal or older, which had been maintained with a lighting cycle of about 12 hours (e.g. ON a 7:00 to 19:00) for about 1 week. When the nonhuman mammal is a female rat (preferably a female Wistar rat), the preferred method for harvesting fertilized eggs generally comprises giving a follicle stimulating hormone in the first place and, after about 48 hours, a luteinizing hormone and mating the animal with a male rat. The dosage of the follicle stimulating hormone may be about 20 to about 50 IU/animal, preferably about 30 IU/animal and the dosage of the luteinizing hormone may be about 0 to about 10 IU/animal, preferably about 5 IU/animal.

By introducing a foreign 25-hydroxyvitamin $D_3$ 24-hydroxylase gene to the harvested fertilized eggs according to the above method, and then artificially transplanting and implanting said fertilized egg in a female nonhuman mammal, a nonhuman mammal which carries a DNA into which a foreign 25-hydroxyvitamin $D_3$ 24-hydroxylase gene or a mutant gene thereof is inserted is obtained.

Another preferred method comprises giving a luteinizing hormone-releasing hormone (generally abbreviated as LHRH) or an analog thereof to a female animal, mating it with a male nonhuman mammal, and implanting the harvested fertilized eggs artificially into the resulting pseudopregnant female nonhuman mammal in which fecundity has been induced.

The dosage of LHRH or an analog thereof and the timing at which the female nonhuman mammal so treated with the hormone is mated with a male partner vary with different kinds of nonhuman mammals. When the nonhuman mammal is a female rat (preferably a female Wistar rat), it is generally advantageous to mate the rat with a male partner on day 4 or thereabout following administration of LHRH or an analog thereof (e.g. [3,5-Dil-$Tyr_5$]-LH-RH, [$Gln_8$]-LH-RH, [D-$Ala_6$]-LH-RH, [des-$Gly_{10}$]-LH-RH, [D-His($Bzl)_6$]-LH-RH, and their ethylamides, etc.). The dosage of LHRH or an analog thereof is generally about 10 to 60 $\mu$g/animal, preferably about 40 $\mu$g/animal.

It is also preferable to use the above method which comprises regulating the sexual cycle of a female nonhuman mammal artificially and harvesting fertilized eggs in combination with the above method which comprises implanting the harvested fertilized eggs artificially in a pseudopregnant female nonhuman mammal with induced fecundity.

The nonhuman mammal which the 25-hydroxyvitamin $D_3$ 24-hydrokylase gene is introduced, of this invention shows a high expression of the 25-hydroxyvitamin $D_3$ 24-hydroxylase gene and as it augments the intrinsic 25-hydroxyvitamin $D_3$ 24-hydroxylase gene function, the animal is liable to develop hypercalcemia, hyperparathyroidism, bone diseases such as rickets, osteomalacia, osteoporosis, dysostonia, etc., renal diseases such as glomerulonephritis, chronic nephritis, renal insufficiency, etc., even joint disease, pulmonary disease, hyperlipidemia, arteriosclerosis, cardiac disease, diabetes, obesity, digestive organ disease, infectious disease, allergic disease, endocrine disease, dementia and/or cancer, and can be used as an animal model for those diseases. For example, by using the mouse or rat of this invention, it is possible to unravel the mechanisms of pathogenesis in hypercalcemia, hyperparathyroidism, bone diseases such as rickets, osteomalacia, osteoporosis, dysostonia, etc., renal diseases such as glomerulonephritis, chronic nephritis, renal insufficiency, etc., even joint disease, pulmonary disease, hyperlipidemia, arteriosclerosis, cardiac disease, diabetes, obesity, digestive organ disease, infectious disease, allergic disease, endocrine disease, dementia, and cancer, explore for prevention and/or treating modalities for those diseases, and perform screenings for candidate compounds for use in the development of drugs for preventing and treating said diseases. Furthermore, as a potential application of the nonhuman mammal which the 25-hydroxyvitamin $D_3$ 24-hydroxylase gene is introduced, of this invention, there can be mentioned the utilization of a mouse with a high expression of the 25-hydroxyvitamin $D_3$ 24-hydroxylase gene as an experimental model for elucidation of the mechanisms of pathogenesis in hypercalcemia, hyperparathyroidism, bone diseases such as rickets, osteomalacia, osteoporosis, dysostonia, etc., renal diseases such as glomerulonephritis, chronic nephritis, renal insufficiency, etc., even joint disease, pulmonary disease, hyperlipidemia, arteriosclerosis, cardiac disease, diabetes, obesity, digestive organ disease, infectious disease, allergic disease, endocrine disease, dementia, or cancer. In this case, the vital functions of 25-hydroxyvitamin $D_3$ 24-hydroxylase will be clarified. It is also expected that the animal can be an experimental model for elucidation of the gene regulating mechanism of the vitamin D receptor which is a nuclear receptor.

The above-described transgenic mammal of this invention can be used as a source of cells for tissue culture as well. Moreover, by direct analysis of the DNA or RNA in the tissue of the transgenic mouse of this invention or analysis of the protein tissue expressed by the gene, the relationship of complicated actions of nuclear receptors to transcription factors can be analyzed. Or by growing cells of a tissue carrying the gene according to the standard tissue culture protocol and using the cultured cells, the functions of cells derived from tissues which are generally not easy to culture, such as bone tissue-derived cells such as osteoblasts and osteoclasts, can be studied. Furthermore, by using the cells, a screening can be made for drugs which would enhance the cell functions. Moreover, as a high-expression cell line becomes available, it is possible to isolate and purify the vitamin $D_3$ 24-hydroxylase and construct the corresponding antibody on a mass scale.

The nonhuman transgenic mammal of this invention provides a model which can be used in the screening for drugs of preventing and/or treating a renal disease, a bone disease, a joint disease, a pulmonary disease, hyperlipidemia, arteriosclerosis, a cardiac disease, diabetes, obesity, a digestive organ disease, an infectious disease, an allergic disease, an endocrine disease, dementia or a cancer. In particular, because the nonhuman transgenic mammal of this invention has a disorder of renal function, it can be used as a model for screenings for drugs of preventing and/or treating diseases of the kidney. Furthermore, because the nonhuman transgenic mammal of this invention shows symptoms of loss of bone mass, it can be used as a model for the screening drugs preventing and/or treating osteoporosis, such as vitamin $D_3$ preparations.

The conventional models of bone disease (rats, mice, etc.) have the following drawbacks relating to species difference, the nonhuman transgenic mammal of this invention is free from those drawbacks and, if only from this point of view, it is a useful animal.

(1) The age-related change in bone mass of rats has a peak just as it is the case with humans.

(2) In rats, the age-related change in bone composition has been well studied.

(3) In alkaline phosphatase and tartaric acid-resistant acid phosphatase (generally abbreviated as TRAP) which are biochemical markers of osteogenesis and bone resorption, significant differences are more frequently observed in rats than in mice. Moreover, bone morphology such as osteometrics can be more easily studied in rats than in mice.

(4) In the fundamental research into bone disease and the screening for the development of therapeutic drugs, rats rather than mice have been used in the majority of instances.

Furthermore, the mammal of this invention is a superior model of renal disease from the following points of view.

(1) Nephrectomized mice and rats are frequently used as models of compromised renal function but since those models are by no means faithfully reflective of the renal disease state, they finds application only in the screening for development and evaluation of limited kinds of therapeutic drugs. In contrast, the transgenic rat of this invention runs a time course of morbidity similar to that of a human with renal disease.

(2) In the transgenic rat of this invention, proteinurea is detected in the juvenile period and the protein level tends to increase with aging. It reflects the disease state in kidney disorders and the relation with biochemical markers as well.

(3) The transgenic rat of this invention is similar to the normal rat in the pattern of body weight gain and in fertility and is easy to use.
(4) There has been no model for glomerulonephritis or IgA nephropathy but the pathological picture of the transgenic rat of this invention resembles the disease state of such disorders.
(5) The conventional hyperlipidemic model rat SHC line and obesity model rat Wister Fatty line also show severe proteinuria and die at the age of about 25 to 30 weeks. However, the transgenic rat of this invention can be used as a model of grave renal disease and can survive up to old age.
(6) The transgenic rat of this invention develops kidney disorders in the juvenile stage and shows progression of the disease state with osteoporosis-like symptoms. Therefore, it is highly useful as a model for a patient with disease of both the kidney and bone.

The nonhuman mammal or a portion thereof which carries DNA into which a foreign 25-hydroxyvitamin $D_3$ 24-hydroxylase gene or a mutant gene thereof is inserted, of this invention, is also useful as an experimental model for the screening for substances (drugs) which can be used for preventing and treating diseases resulting from abnormality of vitamin $D_3$ metabolism, which comprises applying an investigational substance (drug) thereto and assaying the resultant disease state-improving efficacy of the drug in the disease resulting from abnormality of vitamin $D_3$ metabolism. The above-mentioned "disease resulting from abnormality of vitamin $D_3$ metabolism" includes, for example, a renal disease, a bone disease, a joint disease, a pulmonary disease, hyperlipidemia, arteriosclerosis, a cardiac disease, diabetes, obesity, a digestive organ disease, an infectious disease, an allergic disease, an endocrine disease, dementia and a cancer (preferably renal disease and bone disease).

The investigational substance mentioned above includes the known synthetic compounds, peptides and proteins, as well as the tissue extracts, cell culture supernatants or the like from warm-blooded mammals (e.g. mouse, rat, pig, bovine, sheep, monkey, and human). For example, by administering any of said tissue extracts, cell culture supernatants and purification products thereof to the nonhuman transgenic mammal of this invention or adding or otherwise bringing the former into contact with a portion of said mammal (e.g. cells, a tissue or an organ) and assaying the state-improving efficacy in a disease such as renal disease, bone disease, joint disease, pulmonary disease, hyperlipidemia, arteriosclerosis, cardiac disease, diabetes, obesity, digestive organ disease, infectious disease, allergic disease, endocrine disease, dementia or cancer, a screening of candidates (e.g. peptides, proteins, nonpeptide compounds, synthetic compounds, fermentation products, etc.) for drugs of preventing and/or treating can be carried out. Moreover, any substance determined by the screening method of this invention to be efficacious in renal disease, bone disease, joint disease, pulmonary disease, hyperlipidemia, arteriosclerosis, cardiac disease, diabetes, obesity, digestive organ disease, infectious disease, allergic disease, endocrine disease, dementia or cancer (e.g. a 25-hydroxyvitamin $D_3$ 24-hydroxylase inhibitor) will find application for preventing and treating renal disease, bone disease, joint disease, pulmonary disease, hyperlipidemia, arteriosclerosis, cardiac disease, diabetes, obesity, digestive organ disease, infectious disease, allergic disease, endocrine disease, dementia or cancer. Thus, by processing the substance in accordance with the established pharmaceutical procedures, medicinal preparations for preventing and treating renal disease, bone disease, joint disease, pulmonary disease, hyperlipidemia, arteriosclerosis, cardiac disease, diabetes, obesity, digestive organ disease, infectious disease, allergic disease, endocrine disease, dementia or cancer can be provided.

Where, throughout this specification, bases and amino acids are expressed by abbreviations, the abbreviations adopted by IUPAC-IUB Commission on Biochemical Nomenclature or those in common usage in the art are used. The following is a partial list of such abbreviations.

DNA: deoxyribonucleic acid
RNA: ribonucleic acid
A: adenine
T: thymine
G: guanine
C: cytosine The SEQ ID NOs. according to the Sequence listing in this specification denote the following sequences.

SEQ ID NO:1 denotes the nucleotide sequence of one of the primers used for the PCR (polymerase chain reaction) performed in Example 2.

SEQ ID NO:2 denotes the nucleotide sequence of the other primer used for the PCR (polymerase chain reaction) performed in Example 2.

SEQ ID NO:3 denotes the nucleotide sequence of one of the primers used for the PCR (polymerase chain reaction) performed in Example 3.

SEQ ID NO:4 denotes the nucleotide sequence of the other primer used for the PCR (polymerase chain reaction) performed in Example 3.

SEQ ID NO: 5 denotes the nucleotide sequence of one of the primers used for the PCR (polymerase chain reaction) performed in Example 4.

SEQ ID NO:6 denotes the nucleotide sequence of the other primer used for the PCR (polymerase chain reaction) performed in Example 4.

The following examples merely illustrate this invention in further detail and should by no means be construed as defining the scope of the invention.

EXAMPLE 1

1) Construction of the plasmid pMLV-LTR-vitamin $D_3$ 24-hydroxylase carrying a 25-hydroxyvitamin $D_3$ 24-hydroxylase gene downstream of the gene regulatory region of Moloney leukemia virus As Moloney leukemia virus promotor (MLV-LTR), the plasmid pIRA01 derived from plasmid pYJ1, which is described by Goff et al. (1980, Cell, 22, 777), was used. As the terminator (SV40), the terminator sequence contained in said plasmid pcVD1-derived plasmid pIRA01 described by Okayama et al. (1983, Mol. Cell. Biol., 3, 280) and Okayama et al. (1982, Mol. Cell. Biol., 2, 161) was used. The vector for expression of the rat 25-hydroxyvitamin $D_3$ 24-hydroxylase cDNA was constructed as follows. The pUC19-24-hydroxylase described by Ohyama et al. (1991, FEBS Lett., 278, 195) (supplied by professor Tatsuo Suda, Showa University Dental School and Assistant Professor Yoshihiko Ohyama, Hiroshima University School of Physics) was digested with the restriction enzymes EcoRI and Sca I to give a 3.2 kbp fragment containing a rat 25-hydroxyvitamin $D_3$ 24-hydroxylase cDNA. This fragment was further cleaved with P mac I and 100 ng of this pUC19-24-hydroxylase-derived EcoRI-P mac I fragment (2.1 kbp) was treated with calf small intestinal alkaline phosphatase (Takara Shuzo) to dephosphorylate the 5'-end. Then, the multicloning site inserted in Lac Z of the commercial pBluescript II KS(+) was digested with the restriction enzymes SmaI and EcoRI to give a pBluescript II KS(+)-derived SmaI-EcoRI fragment (2.9 kbp). The EcoRI-P mac I fragment (2.1 kbp) derived from pUC19-24-hydroxylase and the SmaI-EcoRI fragment (2.9 kbp) thus derived from pBluescript II KS(+) were ligated using Takara Ligation Kit (Takara Shuzo) at 16° C. for 60 minutes and using this reaction mixture *Escherichia coli* JM109 (Nippon Gene) was transformed to give an ampicillin-resistant strain. From this transformant (*Escherichia coli* JM109/pBluescript II KS(+)-24-hydroxylase), the plasmid DNA was recovered and digested with restriction enzymes to confirm that the EcoRI-P mac I fragment from pUC19-24-hydroxylase had been ligated in the sense orientation within the SmaI-EcoRI fragment derived from pBluescript II KS(+). In this manner, a plasmid, pBluescript II KS(+)-24-hydroxylase (5.0 kbp) was obtained. When this gene construct was analyzed by multiple digestion with restriction enzymes, it contained no detectable transposition.

Then, the pBluescript II KS(+)-24-hydroxylase was digested with the restriction enzymes EcoRI and BamHI to give an EcoRI-BamHI fragment containing the rat 25-hydroxyvitamin $D_3$ 24-hydroxylase cDNA. On the other hand, the MLV-LTR-containing vector pIRA01 was digested with EcoRI and BgI II to give an MLV-LTR-containing EcoRI-BgI II fragment. Then, the above EcoRI-BamHI fragment containing the rat 25-hydroxyvitamin $D_3$ 24-hydroxylase cDNA (derived from pUC-19-24-hydroxylase) was ligated to the above MLV-LTR-containing EcoRI-BgI II fragment using Takara Ligation Kit (Takara Shuzo) at 16° C. for 60 minutes and using this reaction mixture *Escherichia coli* JM109 (Nippon Gene) was transformed to obtain an ampicillin-resistant strain. From this transformant (*Escherichia coli* JM109/pMLV-LTR-vitamin $D_3$ 24-hydroxylase), the plasmid DNA was recovered and digested with restriction enzymes to confirm that the EcoRI-BamHI fragment from pBluescript II KS(+)-24-hydroxylase had been ligated in the sense orientation within the EcoRI-BgI II fragment from pIRA01. In this manner, a plasmid pMLV-LTR-vitamin $D_3$ 24-hydroxylase (6.2 kbp) was obtained. When this gene construct was analyzed by multiple restriction enzyme digestion, it contained no detectable transposition. A schematic diagram showing this plasmid is presented in FIG. 1.

2) Construction of a transgenic rat carrying a fusion gene product containing the 25-hydroxyvitamin $D_3$ 24-hydroxylase gene downstream of the gene regulatory region of Moloney leukemia virus.

Female rats for collection of eggs were purchased at 8 weeks of age and acclimatized for one week using a 12-hour lighting cycle of 7:00 to 19:00. When the rats reached 9 weeks of age, follicle stimulating hormone (pregnant mare serum gonadotropin) (30 IU/animal) was administered intraperitoneally on day 1 at 11:00 and the dosed animals were further maintained under the same conditions as above. On day 3 at 17:00, luteinizing hormone (human chorionic gonadotropin) (5 IU/animal) was administered intraperitoneally and the animals were subjected to cohabitation with male Wistar rats aged 10 weeks or older for mating on a 1:1 basis. On day 4, the female rats were checked for a vaginal plug at 9:00 and starting at 13:30, the animals confirmed to have a vaginal plug was sacrificed and the eggs were harvested. As the fertilized eggs, pronuclear stage eggs were selectively used. At 14:30, the above-mentioned plasmid pMLV-LTR-vitamin $D_3$ 24-hydroxylase was cleaved with ClaI and adjusted to a concentration of 10 μg to 100 μg/ml, and a 1 to 2 μl portion was microinjected into the male pronucleus of the Wistar rat egg in the one-cell stage under microscope-monitoring. The eggs were cultured in HER medium and the 2-cell embryos were confirmed at 13:30 on day 5. Then, in accordance with the protocol described by Wagner et al. (1981, ProNAS, USA, 78, 5016), the embryos were transplanted into the oviduct of pseudopregnant female Wistar rats for implantation.

The pseudopregnant female Wistar rats (11 week-old rat and older) were dosed subcutaneously with luteinizing hormone-releasing hormone or an analog thereof (40 μg/animal) on day 0 at 13:00 and mated with vasoligated male rats of Zucker lean or Wistar strain aged 12 weeks or older on a 1:1 basis on day 4 at 17:00. At 9:00 on day 5, the female rats were confirmed to have a vaginal plug and used for the above purpose.

EXAMPLE 2

Gene analysis of 25-hydroxyvitamin $D_3$ 24-hydroxylase transgenic rats

The gene analysis was performed by the polymerase chain reaction method using the DNA harvested from the tail of the young rat at 3 weeks of age. Thus, the polymerase chain reaction (PCR) was carried out using primer 1 (5'-AGGCTGTGCTGCTAATGTCAA-3': SEQ ID NO:1), which is a 21mer contained in the rat vitamin $D_3$ 24-hydroxylase cDNA, and primer 2 (5'-AAGAGTGGGGGTCAGAGTTCG-3': SEQ ID NO: 2), which is a 21mer in the rat vitamin $D_3$ 24-hydroxylase cDNA. Using 1 μl of the tail DNA preparation, diluted 50-fold with sterile water, as substrate, a PCR was carried out in 1 cycle of 94° C., 3 min. and 25 cycles of 94° C. for 30 sec., 65° C. for 1 min., and 72° C. for 1 min. and the reaction product was electrophoresed through 1.0% agarose GTG (FMC BioProducts) gel and the rats giving a 783 bp DNA band were selected. Analysis of a total of 141 young rats revealed six PCR-positive individuals, one of which was a dead animal.

For the 5 PCR-positive animals, Southern hybridization analysis using the tail DNA preparations was further carried out with (1) a 600 bp digoxigenin-labeled DNA probe containing the rat vitamin $D_3$ 24-hydroxylase gene sequence (labeled by the riboprobe method) or (2) the probe prepared by labeling the 940 bp XbaI/KpnI fragment of rat vitamin $D_3$ 24-hydroxylase cDNA with $^{32}$P-dCTP by the random primer method. In each instance, the tail DNA was digested with PstI/BamHI and the resulting fragment was labeled with $^{32}$P and used as the probe. The DNA for analysis was extracted from an about 1 cm long strip of the tail in accordance with the method described by Horgan et al. (1986, Manipulating the Mouse Embryo (Cold Spring Harbor Laboratory). The nucleic acid pellet obtained was washed in 70% ethanol once, dried and resuspended in 200 μl of 10 mM Tris (pH 8.0)-1 mM EDTA. Moreover, 10 μl each of the DNAs from said 5 PCR-positive and false positive animals was thoroughly digested with the restriction enzymes XhoI and ClaI, electrophoresed through 1.0% agarose GTG gel and introduced onto a nylon filter by the procedure described by Southern (1975, Journal of Molecular Biology, 98, 503). When the riboprobe was used, an overnight hybridization was carried out using this filter as the probe and the reaction product was washed with 2×SSC-0.1% SDS twice at room temperature and then with 0.1×SSC-0.1% SDS twice at 68° C. As the result of Southern hybridization, 4 of the 5 samples tested gave a signal at 1.8 kbp, indicating that the corresponding four rats carried the vitamin $D_3$ 24-hydroxylase gene introduced.

On the other hand, when the probe labeled by the random primer method was used, 10 μg each of DNA preparated from the tail was thoroughly digested with the restriction enzyme NsiI or ClaI, electrophoresed through 1.0% agarose GTG gel and introduced onto a nylon filter in the same manner as above. The filter was treated with prehybridization solution supplemented with 4×SSC-50% formamide-5×Denhart solution-50 μg/ml salmon sperm DNA and 0.2% SDS at 65° C. for 2 hours and then hybridized, same solution supplemented with the probe overnight. The hybridized filter was washed with 1×SSC-0.1% SDS solution at room temperature for 15 minutes for a total of 4 times and then washed with 0.1×SSC-0.1% SDS solution at 68° C. for 15 minutes for a total of 4 times. As the result of this Southern hybridization, one of the 5 samples tested showed a signal at 3.0 kbp, indicating that one of the rats carried the vitamin $D_3$ 24-hydroxylase gene introduced.

Figure 2:
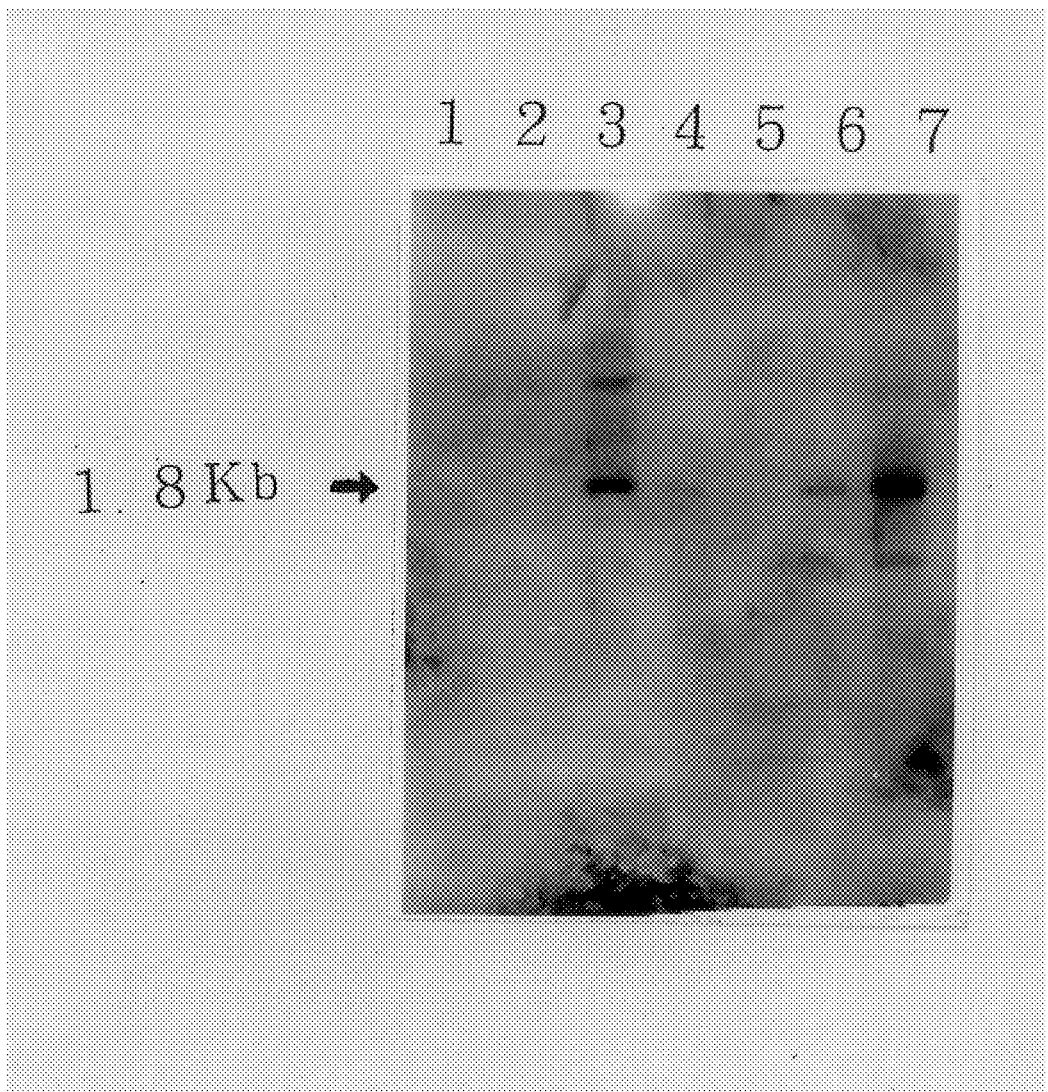
FIG. 2 shows the Southern blots (each sample: 10 μg; alkali blotting) of a transgenic rat using a digoxigenin-labeled 600 bp riboprobe.
Figure 3:
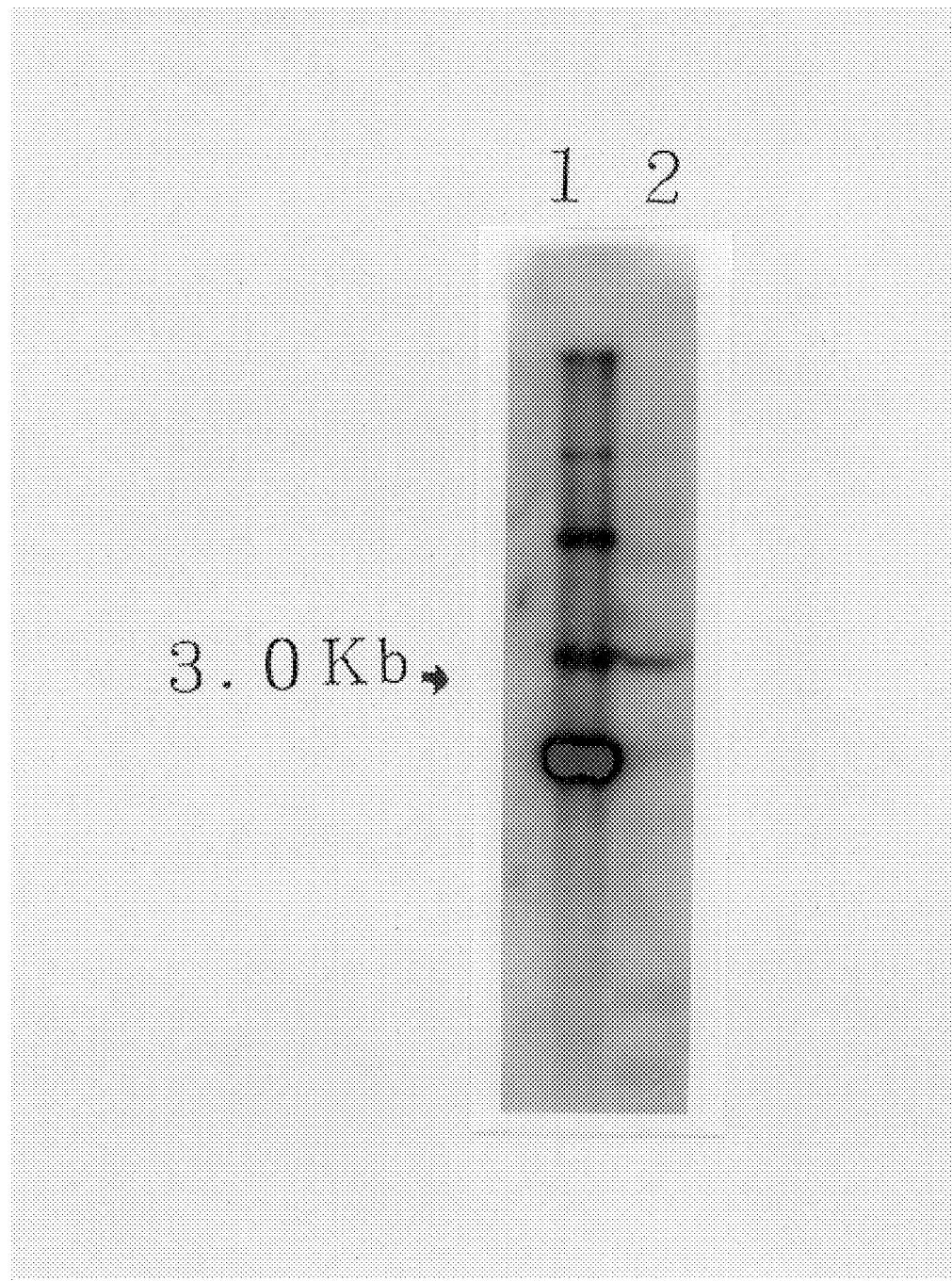
FIG. 3 shows the Southern blots of the transgenic rat using a random primer-labeled XbaI-KpnI 940 bp fragment probe.

As the result of the above Southern analysis, a total of 5 animals were found to carry the 25-hydroxyvitamin $D_3$ 24-hydroxylase gene introduced. The animal numbers of those 5 transgenic animals were R9121-7 (male), R12123-6 (female), R12121-7 (female), R11293-5 (female)and R11293-9 (female). In R10175-9 (male), the introduction of the gene was confirmed by PCR only. (Table 1 and FIGS. 2 and 3).

and the resulting fragment was ligated to the above 3.2 kbp vitamin $D_3$ 24-hydroxylase cDNA-containing fragment using Takara Ligation Kit (Takara Shuzo) at 16° C. for 60 minutes. Using this reaction mixture, *E. coli* JM109 (Nippon Gene) was transformed to give an ampicillin-resistant strain. From this transformant (*Escherichia coli* JM109/pUC119-MLV-24-hydroxylase), the plasmid DNA was recovered and subjected to restriction enzyme cleavage to confirm that a

TABLE 1

Results of transgenic rats production by microinjection of pMLV-LTR-vitamin $D_3$ 24-hydroxylase

| | | Number of oocytes | | Number of rats | | |
|---|---|---|---|---|---|---|
| Transgene | Ex. No. | Number of injected oocytes | Number of transferred embryos | Number of offspring | Number of individuals PCR-analyzed | Number of PCR-positive individuals |
| PMLV-LTR- | 37 | 110 | 63 | 18 | 18 | 1 |
| Vitamin | 38 | 265 | 60 | 17 | 30 | 0 |
| $D_3$ 24- | 39 | 245 | 97 | 21 | 21 | 0 |
| hydroxylase | 40 | 220 | 98 | 36 | 36 | 1 |
| | 41 | 274 | 61 | 24 | 24 | 2 |
| | 42 | 126 | 57 | 18 | 18 | 2 |
| | Total | | 436 | 142 | 141 | 6 |

EXAMPLE 3

1) Cloning of the rat osteocalcin gene promoter

As the rat chromosomal gene regulatory region, the rat osteocalcin gene promoter was prepared by the PCR method using primer 3 (5'-TGAGGACATTACTGACCGCTCCTT-3': SEQ ID NO: 3), which is a 24-mer in rat osteocalcin genomic DNA, and primer 4 (5'-AGTTGCTGTGTGGGACTTGTCTGT-3': SEQ ID NO:4), which is a 24-mer in rat osteocalcin genomic DNA, with reference to the nucleotide sequence data reported by Lian et al. (1989, ProNAS, USA, 86, 1143). The fragment thus obtained was cloned using TA-Cloning Kit. The nucleotide sequence was confirmed in the routine manner using ABI's DNA sequencer.

2) Construction of pOsteocalcin-Vitamin $D_3$-24-hydroxylase, the plasmid having the rat 25-hydroxyvitamin $D_3$ 24-hydroxylase gene downstream of the rat chromosomal gene regulatory region As the terminator (SV40), the terminator sequence contained in the plasmid pcVD1-derived pIRA01 described by Okayama et al. (Mol. Cell. Biol., 3, 280) and Okayama et al. (1982, Mol. Cell. Biol., 2, 161) was used.

The plasmid pPCRII-osteocalcin promotor inserted in the rat osteocalcin gene regulatory region was digested with HindIII and XbaI to give a 600 bp fragment. On the other hand, pUC118 was digested with HindIII and XbaI, and those fragments were ligated using Takara Ligation Kit (Takara Shuzo) at 16° C. for 60 minutes. Using this reaction mixture, *Escherichia coli* JM109 (Nippon Gene) was transformed to give an ampicillin-resistant strain. From this transformant (*Escherichia coli* JM109/pUC118-osteocalcin promoter), the plasmid DNA was recovered and subjected to restriction enzyme cleavage to confirm that a 600 bp fragment had been linked to pUC118. In this manner, a plasmid pUC118-osteocalcin promoter (3.8 kbp) was obtained. This promoter was then digested with the restriction enzymes ScaI and XhoI and the 2.0 kbp ScaI-XhoI fragment was recovered.

The plasmid pMLV-LTR-vitamin $D_3$ 24-hydroxylase (6.2 kbp) obtained in Example 1 was cleaved with ClaI and a 3.2 kbp of vitamin $D_3$ 24-hydroxylase cDNA-containing fragment was recovered. The pUC119 was cleaved with AccI 1500 bp fragment had been ligated to the pUC119. In this manner, a plasmid pUC119-MLV-24-hydroxylase (6.2 kbp) was obtained.

Figure 4:
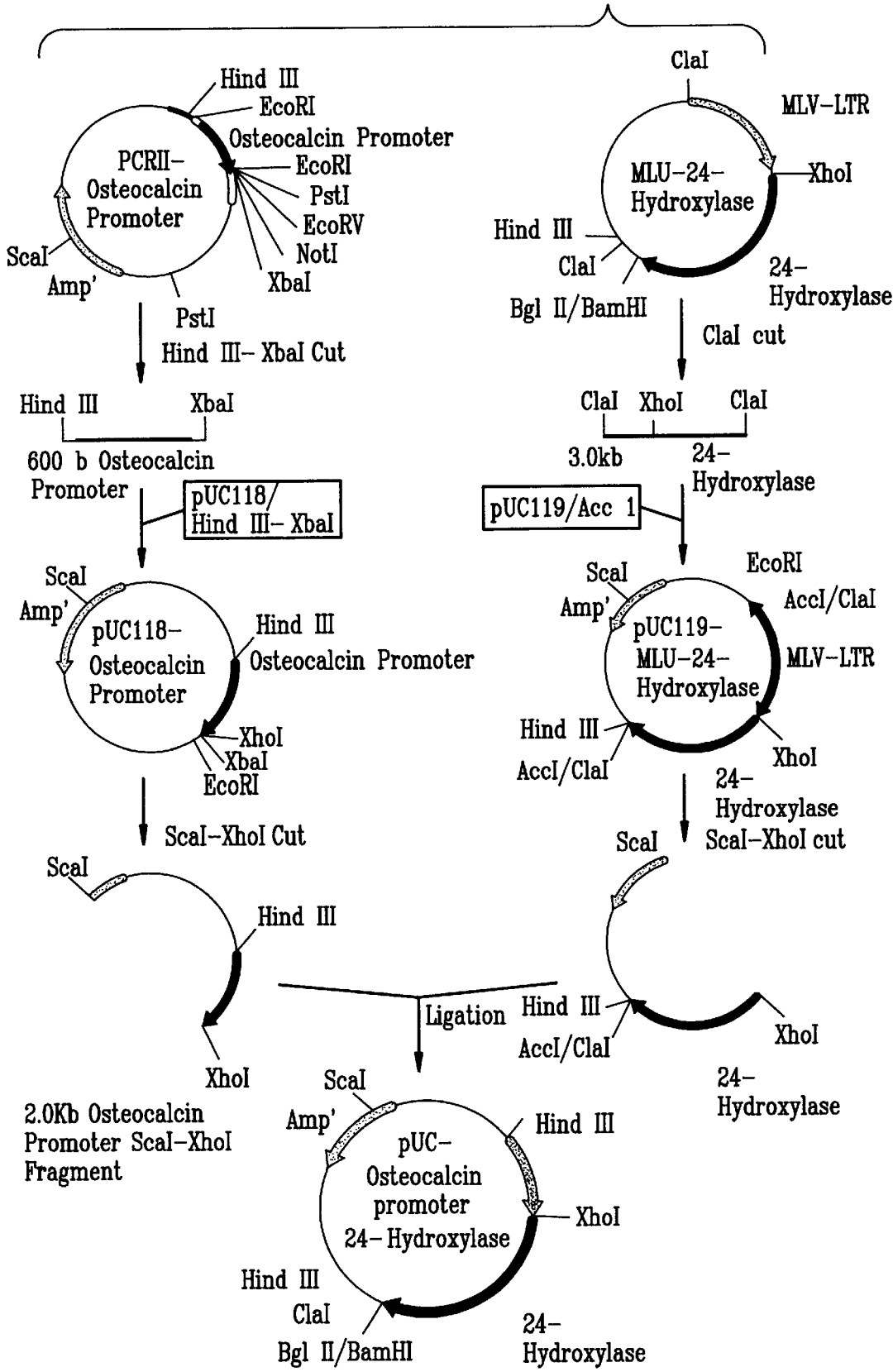
FIG. 4 shows in a schematic diagram showing the construction of the plasmid, pOsteocalcin-Vitamin $D_3$ 24-hydroxylase.

This was further digested with ScaI and XhoI and the 3.8 kbp ScaI-XhoI fragment thus obtained was ligated to the above-mentioned 2.0 kbp ScaI-XhoI fragment using Takara Ligation Kit (Takara Shuzo) at 16° C. for 60 minutes. Using this reaction mixture, *Escherichia coil* JM109 (Nippon Gene) was transformed to give an ampicillin-resistant strain. From this transformant (*Escherichia coil* JM109/pUC-osteocalcin-vitamin $D_3$ 24-hydroxylase), the plasmid DNA was recovered and subjected to restriction enzyme cleavage to confirm that the 1500 bp fragment had been ligated in the sense orientation to pUC119. In this manner, a plasmid pUC-osteocalcin-vitamin $D_3$ 24-hydroxylase (5.8 kbp) was obtained (FIG. 4).

EXAMPLE 4

1) Construction of transgenic rats carrying a fusion gene products having the 25-hydroxyvitamin $D_3$ 24-hydroxylase gene downstream of the rat chromosomal gene regulatory region The gene expression vector containing the 25-hydroxyvitamin $D_3$ 24-hydroxylase gene downstream of the osteocalcin promoter was microinjected into 78 fertilized Wistar/crj rat eggs which were then transferred in 5 pseudopregnant rats. As a result, 17 neonates were obtained but there was no evidence of gene introduction.

The above plasmid pUC-osteocalcin-vitamin $D_3$ 24-hydroxylase was digested with HindIII and ScaI and adjusted to a concentration from 10 µg to 100 µg/ml and a 1 to 2 µl portion was microinjected into the male pronucleus of a fertilized Wistar rat egg in the one-cell stage. The microinjected eggs were transferred into the oviduct of a pseudopregnant female Wistar rat for implantation in accordance with the procedure reported by Wagner et al. (1981, ProNAS, USA, 78, 5016). The eggs were obtained by mating Wistar rats. The Wistar rats were purchased from a commercial source (CLEA JAPAN) and the eggs were grown in foster mother rats until hatching.

The pseudopregnant female Wistar rats (aged 11 weeks or older) were dosed subcutaneously with luteinizing hormone-releasing hormone; generally abbreviated as LHRH) or an analog thereof (40 μg/animal) at 13:00 on day 0. At 17:00 on day 4, those female animals were housed together with vasoligated male Zucker lean or Wistar rats aged 12 weeks or older on a 1:1 basis. At 9:00 on day 5, the female rats which had copulated were checked for a vaginal plug and used for the above purpose.

2) Analysis of the rats into which a foreign rat gene was introduced

Using the DNA harvested from the tail of the young rat at 3 weeks after birth, the gene analysis was carried out by the polymerase chain reaction method. Thus, the PCR was carried out using primer 5 (5'-CTGTCTTCTTTCAACCTGGAT-3': SEQ ID NO:5), which is a 21mer in rat 25-hydroxyvitamin $D_3$ 24-hydroxylase cDNA, and primer 6 (5'-TTAGAGTTCTGTGGGGCATTC-3': SEQ ID NO: 6), which is a 21mer in rat 25-hydroxyvitamin $D_3$ 24-hydroxylase cDNA. Using 1 μl of the tail DNA preparation, diluted 50-fold with sterile water, as substrate, the PCR was carried out in 1 cycle of 94° C., 3 min. followed by 25 cycles of 94° C. for 30 sec., 65° C. for 1 min., 72° C. for 1 min. The reaction product was electrophoresed in 1.0% agarose GTG (FMC Bio-Product) gel and the rats showing a 765 bp DNA band were selected. Analysis of a total of 137 young rats revealed that one of them was PCR-positive. The DNA sample for analysis was prepared by extracting DNA from an about 1 cm long strip of the tail in accordance with the method reported by Horgan et al. (1986, Manipulating the Mouse Embryo (Cold Spring Harbor Laboratory)). The nucleic acid pellet obtained was washed in 70% ethanol once, dried and resuspended in 200 μl of 10 mM Tris(pH 8.0)-1 mM EDTA. As the result of this analysis, the R01163-1 animal was found to be transgenic. The microinjection and gene analysis information is presented in Table 2.

were transgenic. The transgenic rat R10175-9 yielded 12 offspring on Feb. 12, 1995 and one of those offspring was found to be transgenic by PCR gene analysis. The transgenic rat R01163-1 yielded 5 offspring, one of which was found to be transgenic by PCR gene analysis. The transgenic rat R02205-1 gave birth to 12 offspring but none of them were transgenic. Thus, all the transgenic rats but R02205-1 yielded transgenic $F_1$ rats.

Among the multiple-copy transgenic rats, an abnormal animal (R11293-9) weighing 39 g at 5 weeks after birth and having elongated incisors was found but died by accident.

The transgenic rat R12121-7 (female) copulated with one male Wistar rat and gave birth to 12 neonates on the first parturition. The same PCR gene analysis as above revealed that of those offspring were transgenic animals. On the second parturition, 4 offspring were obtained and the same PCR gene analysis revealed that 2 of them were transgenic.

Furthermore, by the brother-sister mating of those $F_1$ animals, i.e. R12121-7-2 (female) and R12121-7-4 (male), born on the second parturition, 15 offspring were obtained.

Gene assay by PCR was carried out and the DNA samples verified to have had the gene introduced were analyzed by Southern blotting in the same manner as above. The sample giving a darker band than the band of the $F_1$ animal was regarded as a homozygote and the sample giving a band of comparable density was regarded as a heterozygote. Further, homozygotes were crossed and the resulting offspring were subjected to the same PCR gene assay as above to confirm that there was no animal failing to give evidence of the gene and based on the result the $F_1$ animals were finally judged to be homozygotes.

As a result, 5 homozygotes, 7 heterozygotes and 3 non-transgenic animals were established.

The homozygotes thus found were R12121-7-2-1 (male), R12121-7-2-3 (female), R12121-7-2-5 (female), R12121-7-

TABLE 2

Results of transgenic rats production by microinjection of pOsteocalcin-Vitamin $D_3$ 24-hydroxylase

| | | Number of oocytes | | Number of rats | | |
|---|---|---|---|---|---|---|
| Transgene | Ex. No. | Number of injected oocytes | Number of transferred embryos | Number of offspring | Number of individuals PCR-analyzed | Number of PCR-positive individuals |
| pOsteocalcin -Vitamin $D_3$ 24-hydroxylase | 43 | 248 | 86 | 19 | 19 | 0 |
| | 44 | 30 | 20 | 8 | 8 | 0 |
| | 45 | 64 | 34 | 6 | 6 | 0 |
| | 46 | 286 | 49 | 24 | 24 | 1 |
| | 47 | 147 | 90 | 35 | 35 | 0 |
| | 48 | 261 | 102 | 45 | 45 | 0 |
| | Total | | 381 | 137 | 137 | 1 |

3) Establishment of a 25-hydroxyvitamin $D_3$ 24-hydroxylase transgenic rat line PCR analysis of the $F_1$ rats of two strains which were found to be transgenic revealed a successful gene transfer in 7 of 17 animals of one strain. For the production of F, progeny of the rats carrying the 25-hydroxyvitamin $D_3$ 24-hydroxylase gene ligated downstream of MLV-LTR, they were mated with male or female Wistar rats on a 1:1 basis.

Figure 5:
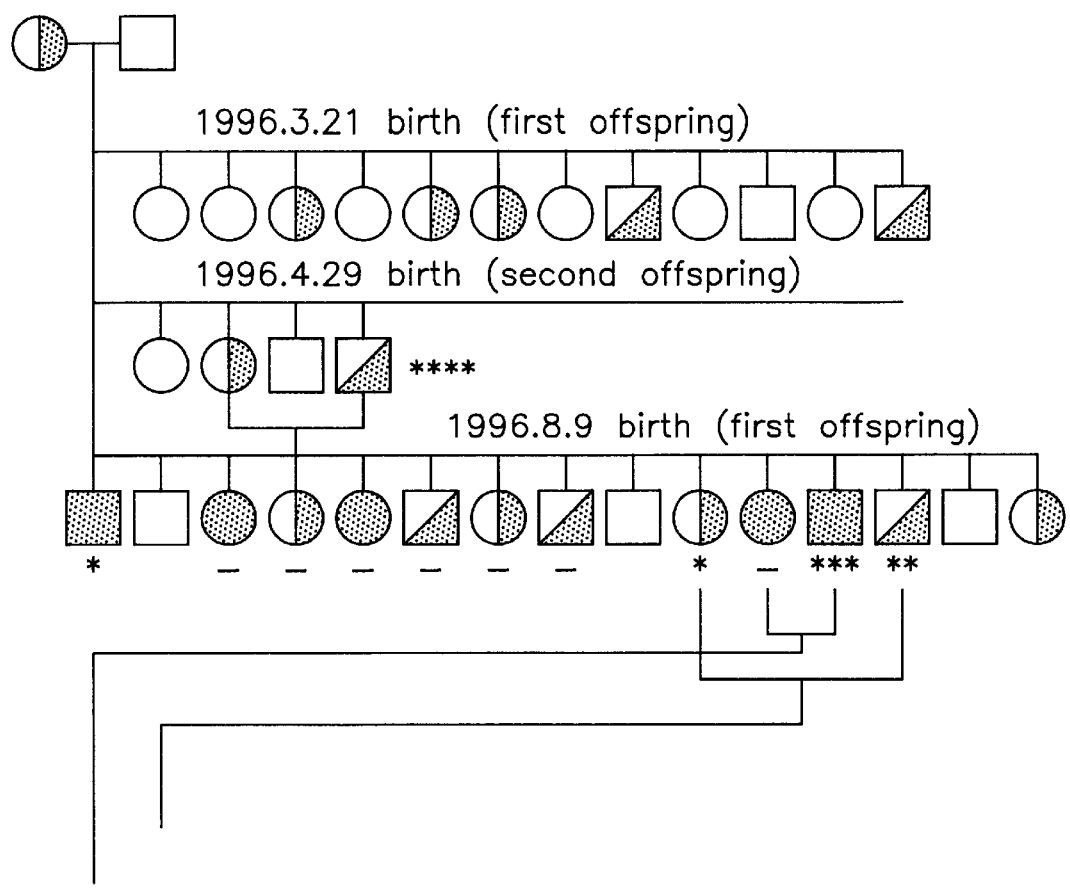
FIG. 5 shows a dendrogram of the transgenic rat R12121-7.

As a result, the transgenic rat R9121-7 yielded 12 $F_1$ animals, 8 of which were found to be transgenic by PCR gene analysis. After the second mating, the same rat yielded 14 offspring, 6 of which were found to be transgenic. The transgenic rat R11293-5 yielded 14 offspring, 6 of which were found transgenic by PCR gene analysis. The transgenic animal R12123-6 gave birth to 11 offspring, 4 of which were found transgenic by PCR gene analysis. After the second mating, the same animal yielded 11 offspring, 3 of which 2-11 (female) and R12121-7-2-12 (male). The dendrogram is presented in FIG. 5.

EXAMPLE 5

Characteristics of 25-hydroxyvitamin $D_3$ 24-hydroxylase transgenic rats

1) Quantitation of vitamin $D_3$ metabolites in the blood of transgenic rats

The vitamin $D_3$ fractions of a transgenic rat were assayed and an attempt was made to construct rats with vitamin D deficiency for the purpose of investigating the degree of expression of the introduced gene. First, the transgenic rat immediately after weaning at 3 weeks old and its litter mates were fed on AIN-93G pure food (Oriental Yeast Co.) from which vitamin D had been removed and Ca and P adjusted to 0.5% and 0.6%, respectively, with deionized water made available in an animal room protected from light with acrylic resin plates for 1 week. Then, using AIN-93G pure food (Oriental Yeast Co.) from which vitamin D had been removed and Ca and P adjusted to 0.03% and 0.15%, respectively, and deionized water, the animals were maintained in the same environment for 4 weeks. On the last day of the 8th week after birth, 2 ml of blood was drawn for vitamin D assay and the serum was separated in the routine manner. The assay was performed in accordance with the method described in the literature, e.g. The Vitamin Society of Japan (edited and authored, 1989): Vitamin Handbook (3) (Kagaku Dojin). The body weights of the respective animals were recorded on a weekly basis throughout the period of feeding with the vitamin D-deficient, low-calcium food.

As a result, the body weights of the R9121-7 $F_1$ female transgenic rats at 8 week of age on vitamin-deficient, low-calcium diet were 135 to 167 g, while the body weights of the female non-transgenic rats were 139 to 157 g. On the other hand, the body weights of the R9121-7 $F_1$ female transgenic rats at week 8 on normal diet were 206 to 224 g, while the body weights of the female non-transgenic rats were 196 g.

The quantitation of various vitamin $D_3$ metabolites showed no remarkable difference in the serum levels of 1α,25-dihydroxyvitamin $D_3$, 24,25-dihydroxyvitamin $D_3$ and 25-hydroxyvitamin $D_3$ between the transgenic rat and non-transgenic rat fed on vitamin D-deficient, low-calcium diet. Thus, there was no effect attributable to feeding with vitamin D-deficient, low-calcium food.

On the other hand, when the rats were fed on normal diet, the level of 24,25-hydroxyvitamin $D_3$ was not less than 10.0 ng/ml in 3 of the 4 transgenic rats but the level in the non-transgenic rats was 7 to 9 ng/ml. In the level of 25-hydroxyvitamin $D_3$, the individual values were within the range of 19 to 13 ng/ml, thus showing no difference. The level of 1α,25-dihydroxyvitamin $D_3$ was 130 pg/ml to 89 pg/ml in the non-transgenic rats versus 54 to 11 ng/ml in the transgenic rats (Table 3).

TABLE 3

Quantitation of each vitamin $D_3$ metabolite of Vitamin D-deficient transgenic rat

| Diet condition | 25(OH) Vitamin $D_3$ | 24,25(OH) Vitamin $D_3$ | 1α, 25(OH) Vitamin $D_3$ |
|---|---|---|---|
| Vitamin D-deficient diet | | | |
| No. 1 transgenic ♀ | <3 ng/ml | 1.1 ng/ml | 30 pg/ml |
| 2 transgenic ♀ | <2 | <0.7 | 65 |
| 11 transgenic ♀ | <3 | <0.8 | 95 |
| 3 non-transgenid ♀ | <3 | <0.9 | 81 |
| 4 non-transgenic ♀ | <3 | <0.8 | 77 |
| 6 non-transgenic ♀ | <3 | <0.9 | 75 |
| Normal diet | | | |
| No. 7 transgenic ♀ | 19 | 10.9 | 37 |
| 12 transgenic ♀ | 14 | 8.3 | 39 |
| No. 13 non-transgenic ♀ | 17 | 7.7 | 130 |
| 14 non-transgenic ♀ | 17 | 8.7 | 89 |
| R9121-7 transgenic ♂ | 13 | 11.1 | 11 |
| R10195-9 transgenic ♂ | 15 | 10.6 | 54 |

2) Quantitation of vitamin $D_3$ metabolites in the blood of transgenic rats fed on normal diet The vitamin $D_3$ metabolites in the blood were respectively assayed in 5 female $F_0$ transgenic rats carrying the 25-hydroxyvitamin $D_3$ 24-hydroxylase gene introduced, namely R02205-1, R12123-6, R12121-7, R01163-1 and R11293-5 ($F_0$ animals, from 20 to 40 weeks old), two R12121-7 $F_1$ transgenic rats, and two non-transgenic rats. As a result, the serum levels of 25-hydroxyvitamin $D_3$ in the transgenic rats were found to be 28 to 10 ng/ml. While the 24,25-dihydroxyvitamin $D_3$ level was higher than 10.0 ng/ml in the transgenic rats R12123-6, R01163-1 and R11293-5, the other two transgenic rats showed lower levels. As to R12121-7 $F_1$ animals, two females gave values in excess of 10.0 ng/ml but two males showed lower levels. The 1α,25-hydroxyvitamin $D_3$ level was higher than 100 pg/m in the transgenic rats R02205-1 and R12121-7 and non-transgenic $F_1$ male animal R12121-7-3. Thus, the animals showing high levels of 24,25-dihydroxyvitamin $D_3$ showed low levels of 1α,25-dihydroxyvitamin $D_3$. Among transgenic rats, large individual differences were found in the blood levels of vitamin $D_3$ metabolites (Table 4).

TABLE 4

Quantitation of each vitamin $D_3$ metabolite of transgenic rat

Diet condition (normal diet)

| Individual Number | | 25(OH) Vitamin $D_3$ | 24,25(OH) Vitamin $D_3$ | 1α, 25(OH) Vitamin $D_3$ |
|---|---|---|---|---|
| 1) R12121-7-1 | $F_1$ ♀ | 21 ng/ml | 13.9 ng/ml | 8 pg/ml |
| 2) R12121-7-2 | $F_1$ transgenic ♀ | 28 | 12.0 | 7 |
| 3) R12121-7-3 | $F_1$ ♂ | 21 | 7.7 | 110 |
| 4) R12121-7-4 | $F_1$ transgenic ♂ | 10 | 3.9 | 82 |
| 5) R11293-5 | $F_0$ transgenic ♀ | 17 | 12.2 | 25 |
| 6) R12121-7 | $F_0$ transgenic ♀ | 20 | 4.7 | 125 |
| 7) R12123-6 | $F_0$ transgenic ♀ | 16 | 11.0 | 52 |
| 8) R02205-1 | $F_0$ transgenic ♀ | 25 | 6.5 | 195 |
| 9) R01163-1 | $F_0$ transgenic ♀ | 18 | 13.2 | 13 |

3) Acquisition of an abnormal transgenic rat

Figure 6:
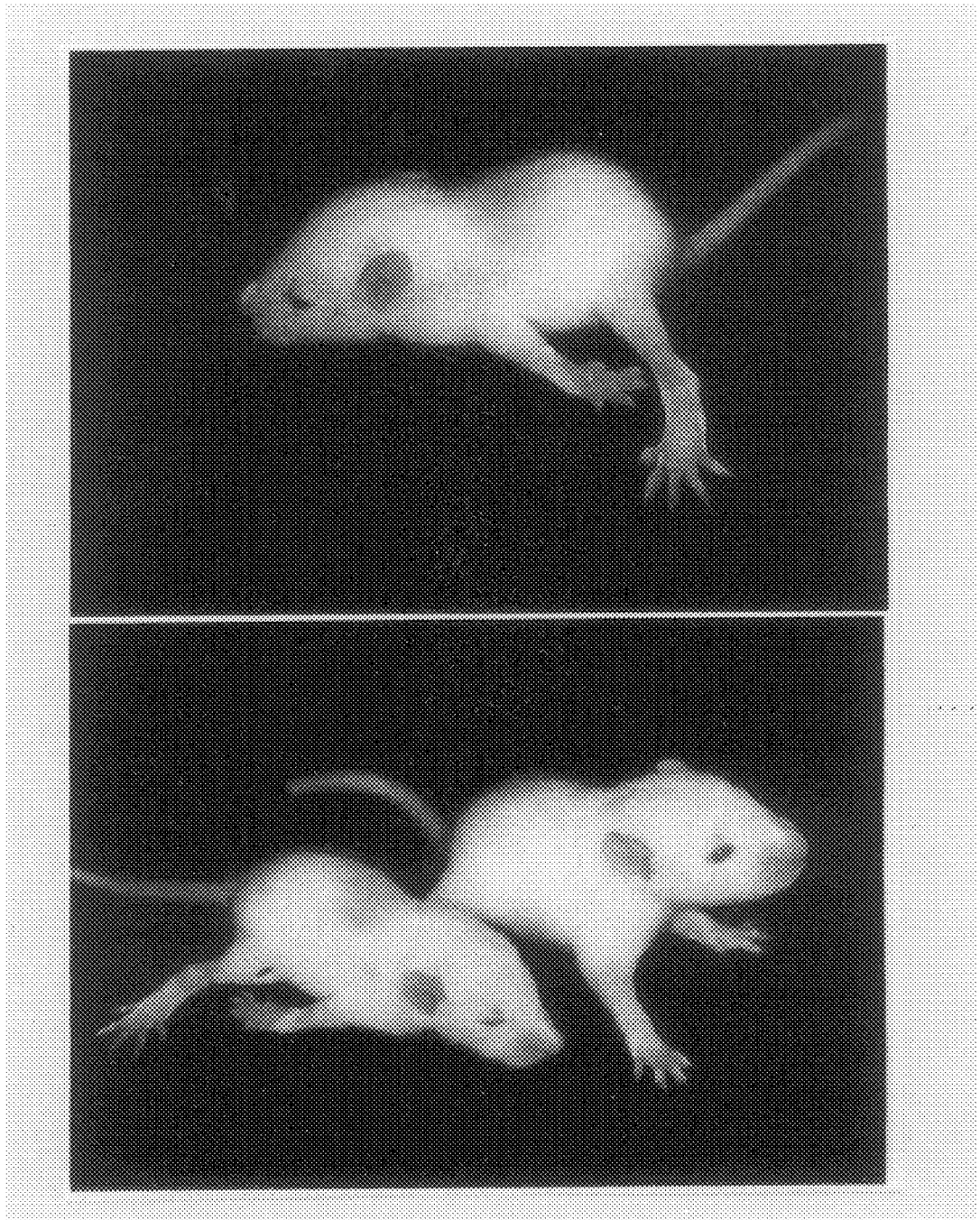
FIG. 6 shows an abnormal individual (15-day old rat) among the rats carrying the MLV-LTR-Vitamin $D_3$ 24-hydroxylase gene introduced.

Among the 12121-7 $F_1$ transgenic rats, a female animal (Animal No. 12121-7-3) was emaciated and had quadriplegia, knee bend disorder, and marked abnormal gait after birth in contrast with the other transgenic rats and its litter mates. This animal weighed 12 g on day 15 after birth, thus being considerably underweight as compared with the other female transgenic rats which weighed 19 to 21 g or its litter mates which weighed 17 to 23 g (FIG. 6). Comparison of this animal with its litter mates revealed no morphologic abnormalities in the bones and dents. This animal died on day 17 after birth.

Figure 7:
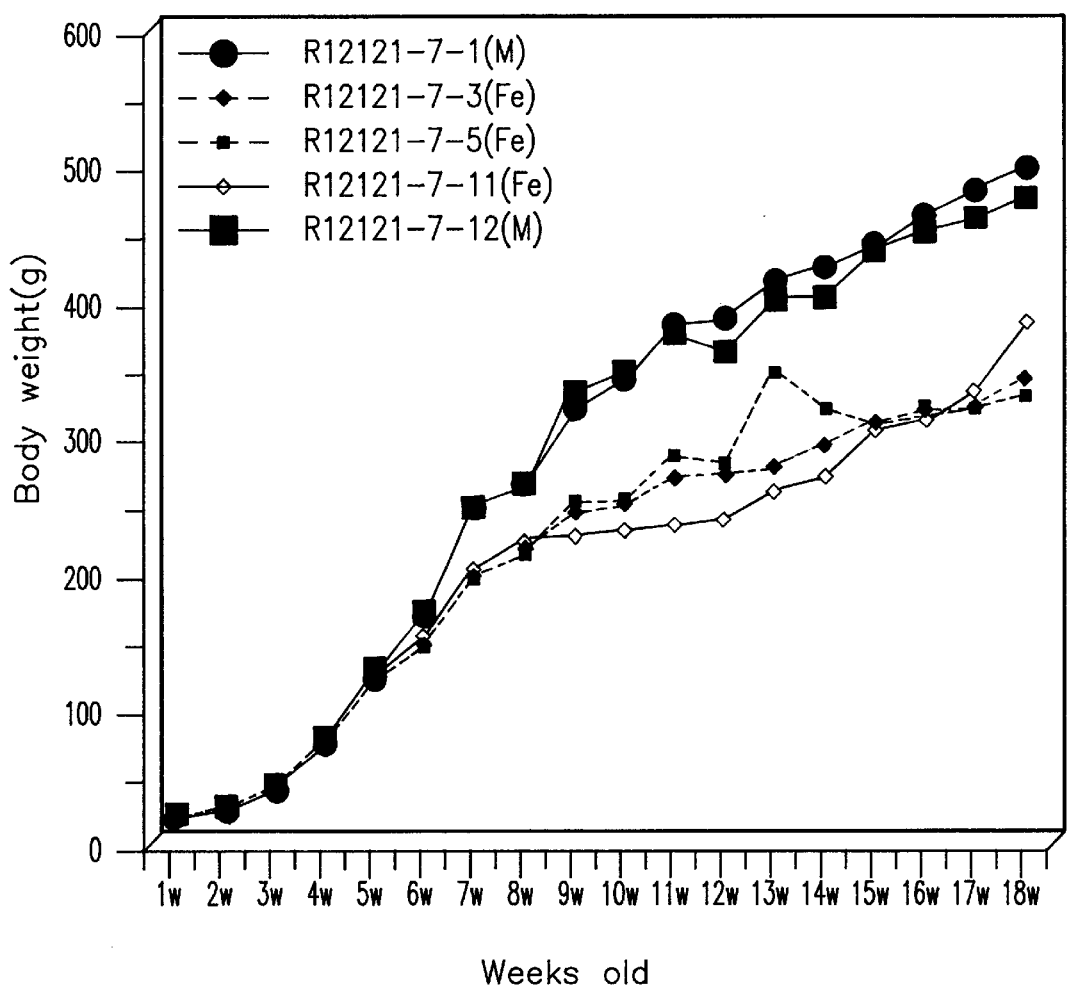
FIG. 7 is a diagram showing the time course of body weight of a transgenic rat, R12121-$7F_2$ (homozygote).
Figure 8:
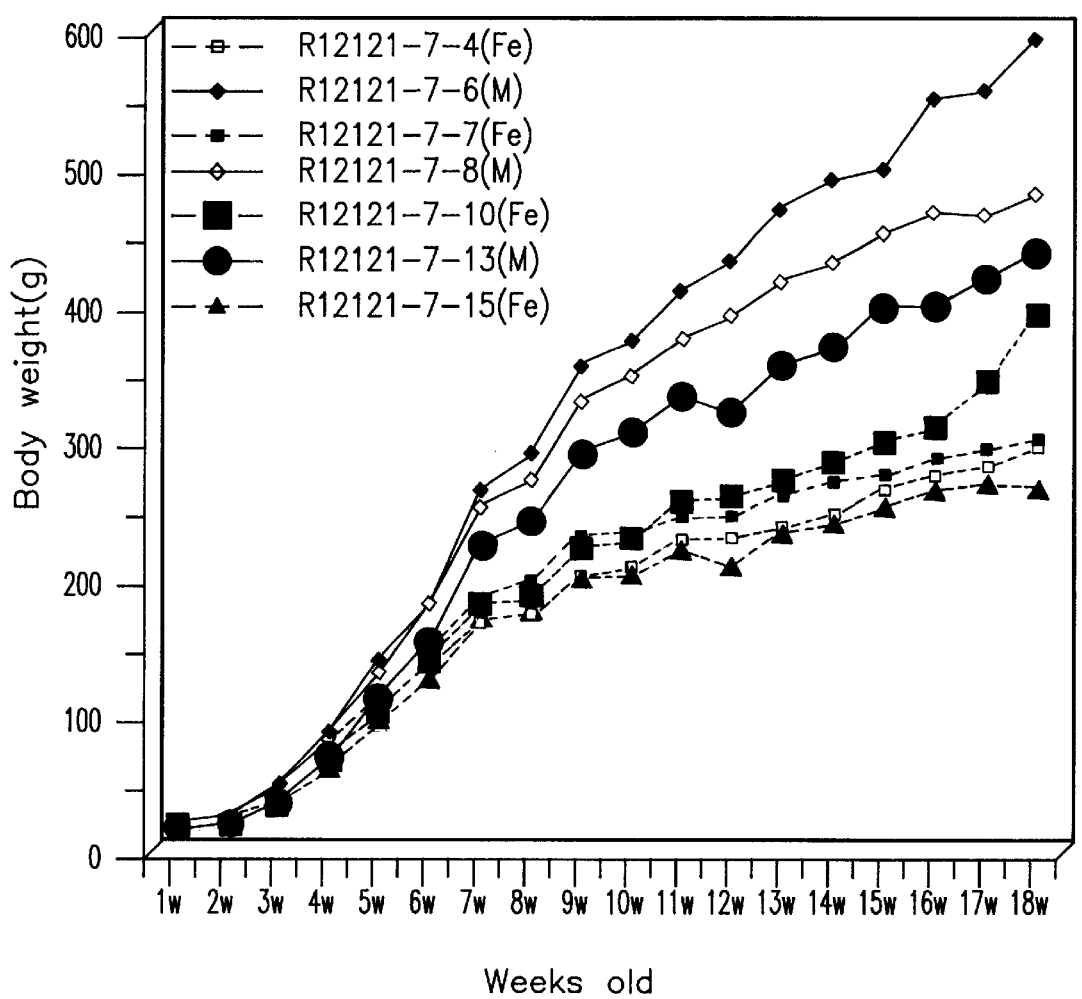
FIG. 8 is a diagram showing the time course of body weight of a transgenic R12121-$7F_2$ (heterozygote).

4) Changes in the body weights of 25-hydroxyvitamin $D_3$ 24-hydroxylase transgenic rats The body weights of heterozygotes and homozygotes among animals of $F_2$ generation of the transgenic rat R12121-7 line were recorded up to week 18 after birth. As a result, the homozygotes and heterozygotes also showed a tendency toward week-by-week increase in body weight. At week 6 and onward, a definite difference was found between male and female animals for each kind of zygote and the body weights of homozygotes at week 18 were 450 to 500 g for males versus 300 to 350 g for females and the body weights of heterozygotes were 450 to 600 g for males versus 250 to 400 g for females. No abnormality was found in any of the animals investigated (FIGS. 7 and 8).

5) Urinalysis of 25-hydroxyvitamin $D_3$ 24-hydroxylase transgenic rats

For the determination of urinary albumin and urinary creatinine levels, the 24-hour urine of each transgenic rat was collected using a metabolism cage. The assay of urinary albumin was carried out colorimetrically using the commercial kit A/G, B-Test Wako (Wako Pure Chemical Ind.)in the routine manner. Urinary creatinine was determined colorimerically using the commercial kit Creatinine HA-Test Wako HA7050 (Wako Pure Chemical Ind.) in the routine manner. In addition, the urinary albumin/urinary creatinine ratio was calculated from measured values for each animal.

As a result, among the transgenic rats of $F_0$ generation, the R12123-6 (female) showed high urinary albumin levels, i.e. 129 mg/day at week 41, 161 mg/day at week 44, and 214 mg/day at week 47, and even still higher values week after week. The other transgenic rats showed values ranging from 7.5 to 37 mg/day and no remarkable difference between weeks in any individual. As to urinary creatinine, transgenic rats showed values ranging from 9.3 to 24.7 mg/day, varying from one individual to another, but there was no week-to-week difference within any individual. Regarding the urinary albumin/urinary creatinine ratio of each animal, the ratio in R12123-6 (female) was 13.6 at week 41, 16.4 at week 44 and 21.7 at week 47 and increased further week by week thereafter. The other transgenic rats gave values ranging from 0.31 to 2.47 (Table 5).

TABLE 5

Urinary analysis in transgenic rat

| Individual No. | Sex | Generation | Age | Albumin (mg/day) | Creatine (mg/day) | Alb/Crea |
|---|---|---|---|---|---|---|
| R9121-7 | ♂ | $F_0$ | 52 | 26.1 | 16.5 | 1.58 |
|  |  |  | 55 | 29.1 | 16.4 | 1.77 |
|  |  |  | 58 | 37.0 | 15.0 | 2.47 |
| R10175-9 | ♂ | $F_0$ | 48 | 26.1 | 24.7 | 1.06 |
|  |  |  | 51 | 28.9 | 23.8 | 1.21 |
|  |  |  | 54 | 7.51 | 24.3 | 0.31 |
| R11293-5 | ♀ | $F_0$ | 44 | 11.0 | 10.2 | 1.08 |
|  |  |  | 47 | 8.0 | 11.9 | 0.67 |
|  |  |  | 50 | 14.8 | 11.3 | 1.31 |
| R12121-7 | ♀ | $F_0$ | 41 | 6.50 | 7.60 | 0.85 |
|  |  |  | 44 | 4.80 | 10.6 | 0.45 |
|  |  |  | 47 | 7.05 | 9.33 | 1.31 |
| R12123-6 | ♀ | $F_0$ | 41 | 129 | 9.50 | 13.6 |
|  |  |  | 44 | 161 | 9.80 | 16.4 |
|  |  |  | 47 | 214 | 9.86 | 21.7 |
| R01163-1 | ♀ | $F_0$ | 36 | 10.7 | 10.0 | 1.07 |
|  |  |  | 39 | 8.70 | 10.5 | 0.83 |
|  |  |  | 42 | 8.10 | 10.6 | 0.76 |
| R02205-1 | ♀ | $F_0$ | 32 | 8.30 | 11.6 | 0.72 |
|  |  |  | 35 | 10.3 | 11.1 | 0.93 |
|  |  |  | 38 | 16.8 | 13.1 | 1.28 |

With regard to the urinary albumin concentration in the transgenic rats of $F_1$ generation, R12121-7-4 (male) gave high values, i.e. 372 mg/day at 26 weeks old, 352 mg/day at 29 weeks old and 311 mg/day at 31 weeks old. As to the other transgenic rats of $F_1$ generation, R12123-6-3 (male) and R12123-6-9 (male) gave the values 19 to 28.6 mg/day and the level in R12123-6-5 (female) was about 11 mg/day. The range of urinary creatinine concentration in the transgenic rats of $F_1$ generation was 7.8 to 26.2 mg/day. Regarding the urinary albumin/urinary creatinine ratio in each individual, R12121-7-4 (male) showed high values, i.e. 26.6 at 26 weeks old, 21.5 at 29 weeks old and 24.5 at 31 weeks old and the other transgenic rats of $F_1$ generation gave values within the range of 0.45 to 2.1 (Table 6).

TABLE 6

Urinary analysis in $F_1$ generation of transgenic rat

| Individual No. | Sex | Generation | Age | Albumin (mg/day) | Creatine (mg/day) | Alb/Crea |
|---|---|---|---|---|---|---|
| R12121-7-4 | ♂ | $F_1$ | 26 | 372 | 14.0 | 26.6 |
|  |  |  | 29 | 352 | 16.4 | 21.5 |
|  |  |  | 32 | 311 | 12.7 | 24.5 |
| R12123-6-3 | ♂ | $F_1$ | 23 | 26.5 | 15.7 | 1.69 |
|  |  |  | 26 | 22.8 | 16.8 | 1.36 |
|  |  |  | 29 | 20.5 | 21.6 | 0.95 |
| R12123-6-5 | ♀ | $F_1$ | 23 | 11.3 | 8.00 | 1.41 |
|  |  |  | 26 | 11.6 | 7.84 | 1.48 |
|  |  |  | 29 | 11.9 | 26.2 | 0.45 |
| R12123-6-9 | ♂ | $F_1$ | 23 | 28.6 | 13.6 | 2.10 |
|  |  |  | 26 | 19.3 | 10.8 | 1.79 |
|  |  |  | 29 | 27.1 | 14.4 | 1.88 |

With regard to urinary albumin, the transgenic rat $F_2$ homozygote R12121-7-12 (male) gave values over 110 mg/day at and after week 11 and the R12121-7-l $F_2$ homozygote (male) showed values over 30 mg/day. However, the range in the other 3 female homozogotes was from 4 to 10 mg/day. As to the heterozygotes, R12121-7-13 (male) showed values over 80 mg/day at and after 11 weeks old and R12121-7-10 (female) gave values around 20 mg/day but the range in the other heterozygotes was from 10 to 19 mg/day in 2 males and from 5 to 15 mg/day in 3 females. In control rats, the mean of 5 males was 12.3 mg/day and the mean of 5 females was 7.7 mg/day. As regards urinary creatinine in homozygotes, the concentration range in two males was from 10 to 15 mg/day and that in 3 females was from 7 to 11 mg/day. Among the heterozygotes, 3 males gave values within the range of 8 to 16 mg/day and 4 females from 5 to 10 mg/day. In control rats, the mean of 5 males was 13.5 mg/day and the mean of 5 females was 9.2 mg/day. As to the urinary albumin/urinary creatinine ratio of each individual animal, the ratio in the homozygote R12121-7-12 (male) was over 8.0 and that in R12121-7-1 (male) was over 2.8. However, the range in the other 3 female homozygotes was 0.5 to 1.3. Among the heterozygotes, the ratio in R12121-7-13 (male) was in excess of 9.0 and that in R12121-7-10 (female) was over 2.4. The values in the other heterozygotes were 0.9 to 1.8 in 2 males and 0.8 to 2.4 in 3 females. In control rats, the mean of 5 males was 0.9 and the mean of 5 females was 0.8 (Table 7).

TABLE 7

Urinary analysis in $F_2$ generation of transgenic rat
Line; R12121-7 derived $F_2$ generation (heterozygote and homozygote)

| Individual No. | Sex | 11w | 14w | 17w | 21w | 24w | 27w | 30w |
|---|---|---|---|---|---|---|---|---|
|  |  | Albumin (mg/day) | | | | | | |
| Albumin content Heterozygote |  |  |  |  |  |  |  |  |
| 7-4 | ♀ | 5.9 | 6.6 | 9.4 | 3.6. | 8.7 | 16.2 | 9.3 |
| 7-6 | ♂ | 16.3 | 18.3 | 10.8 | — | — | — | — |

TABLE 7-continued

Urinary analysis in $F_2$ generation of transgenic rat
Line; R12121-7 derived $F_2$ generation (heterozygote and homozygote)

| Individual No. | Sex | 11w | 14w | 17w | 21w | 24w | 27w | 30w |
|---|---|---|---|---|---|---|---|---|
| 7-7 | ♀ | 14.9 | 10.1 | 7.5 | 8.6 | 13.5 | 28.9 | 23.9 |
| 7-8 | ♂ | 18.1 | 15.7 | 14.1 | 19.7 | 16.4 | 23.5 | 18.0 |
| 7-10 | ♀ | 23.1 | 17.0 | 28.9 | 48.5 | 60.5 | 54.8 | 52.4 |
| 7-13 | ♂ | 88.0 | 84.5 | 115.8 | 198.0 | 210.0 | 341.2 | 303.7 |
| 7-15 | ♀ | 11.3 | 14.5 | 11.2 | 21.1 | 24.6 | 57.2 | 42.1 |
| Homozygote | | | | | | | | |
| 7-1 | ♂ | 32.0 | 39.4 | 77.3 | 124.5 | 244.0 | 370.0 | — |
| 7-3 | ♀ | 5.4 | 9.1 | 6.4 | 17.5 | 11.8 | 18.6 | 12.6 |
| 7-5 | ♀ | 9.1 | 9.9 | 4.9 | 8.8 | 7.6 | 11.5 | 11.1 |
| 7-11 | ♀ | 9.0 | 9.4 | 4.6 | 7.1 | 10.5 | 21.1 | 10.9 |
| 7-12 | ♂ | 118.0 | 120.0 | 169.0 | 277.3 | 343.0 | 441.3 | 439.4 |
| Control | | | | | | | | |
| 1 | ♂ | 14.6 | 13.0 | 31.4 | 9.3 | 36.6 | 22.4 | |
| 2 | ♂ | 11.8 | 21.7 | 13.7 | 11.6 | 22.1 | 15.6 | |
| 3 | ♂ | 13.9 | 13.4 | 11.2 | 10.3 | 16.9 | 6.8 | |
| 4 | ♂ | 7.2 | 9.3 | 24.1 | 13.8 | 17.0 | 8.1 | |
| 5 | ♂ | 14.1 | 12.6 | 20.4 | 14.6 | 29.5 | 3.9 | |
| Mean ± S.D. | | 12.3 ± 3.1 | 14.0 ± 4.6 | 20.2 ± 8.1 | 11.9 ± 2.3 | 24.4 ± 8.5 | 11.4 ± 7.5 | |
| Control | | | | | | | | |
| 1 | ♀ | 5.6 | 13.4 | 7.7 | 9.4 | 16.2 | 6.1 | |
| 2 | ♀ | 10.6 | 7.5 | 9.1 | 12.3 | 5.5 | 29.1 | |
| 3 | ♀ | 9.7 | 10.1 | 4.0 | 8.0 | 22.7 | 14.6 | |
| 4 | ♀ | 5.6 | 4.2 | 13.9 | 4.5 | 17.7 | 13.1 | |
| 5 | ♀ | 7.1 | 6.9 | 11.2 | 7.1 | 19.6 | 49.6 | |
| Mean ± S.D. | | 7.7 ± 2.3 | 8.4 ± 3.5 | 9.2 ± 3.7 | 8.3 ± 2.9 | 17.8 ± 8.1 | 22.5 ± 17.3 | |
| | | | | | Creatinine (mg/day) | | | |
| Creatinine content | | | | | | | | |
| Heterozygote | | | | | | | | |
| 7-4 | ♀ | 5.9 | 8.0 | 7.7 | 8.6 | 13.4 | 8.8 | 7.3 |
| 7-6 | ♂ | 11.4 | 16.0 | 11.2 | — | — | — | — |
| 7-7 | ♀ | 6.2 | 8.5 | 8.3 | 9.9 | 8.6 | 8.4 | 9.0 |
| 7-8 | ♂ | 10.4 | 13.9 | 11.8 | 16.9 | 16.4 | 17.2 | 14.7 |
| 7-10 | ♀ | 7.0 | 9.4 | 11.0 | 9.0 | 9.4 | 8.8 | |
| 7-13 | ♂ | 8.3 | 9.3 | 12.1 | 12.4 | 9.5 | 16.7 | 15.6 |
| 7-15 | ♀ | 5.9 | 7.2 | 7.4 | 12.4 | 7.7 | 6.9 | 6.2 |
| Homozygote | | | | | | | | |
| 7-1 | ♂ | 10.7 | 13.8 | 17.8 | 14.2 | 13.4 | 13.2 | — |
| 7-3 | ♀ | 8.9 | 10.5 | 16.7 | 10.9 | 11.2 | 10.4 | 9.3 |
| 7-5 | ♀ | 9.0 | 10.5 | 20.3 | 10.7 | 9.8 | 9.9 | |
| 7-11 | ♀ | 7.2 | 8.8 | 16.5 | 12.1 | 11.4 | 9.8 | 7.9 |
| 7-12 | ♂ | 12.9 | 14.4 | 15.1 | 16.3 | 13.9 | 17.4 | 15.6 |
| Control | | | | | | | | |
| 1 | ♂ | 13.9 | 18.0 | 17.8 | 21.0 | 18.6 | 15.4 | |
| 2 | ♂ | 12.3 | 21.2 | 16.7 | 16.7 | 16.7 | 12.4 | |
| 3 | ♂ | 14.7 | 43.4 | 20.3 | 18.9 | 20.7 | 9.0 | |
| 4 | ♂ | 11.5 | 14.2 | 16.5 | 16.1 | 15.5 | 19.0 | |
| 5 | ♂ | 15.2 | 16.8 | 15.1 | 19.1 | 13.7 | 5.2 | |
| Mean ± S.D. | | 13.5 ± 1.6 | 22.7 ± 11.8 | 17.3 ± 1.9 | 18.4 ± 2.0 | 17.0 ± 2.7 | 12.2 ± 5.4 | |
| Control | | | | | | | | |
| 1 | ♀ | 10.4 | 10.2 | 11.9 | 11.5 | 10.0 | 11.4 | |
| 2 | ♀ | 10.1 | 11.5 | 4.4 | 11.5 | 10.3 | 19.5 | |
| 3 | ♀ | 10.9 | 11.3 | 8.8 | 11.4 | 11.5 | 27.2 | |
| 4 | ♀ | 7.1 | 5.5 | 11.2 | 9.5 | 9.1 | 8.5 | |
| 5 | ♀ | 7.5 | 10.7 | 10.4 | 9.9 | 10.9 | 35.4 | |
| Mean ± S.D. | | 9.2 ± 1.8 | 9.8 ± 2.5 | 9.3 ± 3.0 | 10.8 ± 1.0 | 10.4 ± 1.3 | 20.4 ± 11.1 | |
| | | | | | Albumin/Creatinine | | | |
| Albumin content/Creatinine content | | | | | | | | |
| Heterozygote | | | | | | | | |
| 7-4 | ♀ | 1.00 | 0.83 | 0.80 | 0.42 | 0.65 | 1.84 | 1.27 |
| 7-6 | ♂ | 1.43 | 1.14 | 0.96 | — | — | — | — |
| 7-7 | ♀ | 2.40 | 1.19 | 0.90 | 0.87 | 1.57 | 3.44 | 2.66 |
| 7-8 | ♂ | 1.74 | 1.13 | 1.19 | 1.17 | 1.00 | 1.37 | 1.22 |
| 7-10 | ♀ | 3.92 | 2.45 | 3.07 | 4.41 | 6.72 | 5.83 | 5.95 |
| 7-13 | ♂ | 10.6 | 9.11 | 9.57 | 16.0 | 22.1 | 20.4 | 19.5 |
| 7-15 | ♀ | 1.92 | 2.02 | 1.52 | 3.35 | 3.19 | 8.3 | 6.79 |

TABLE 7-continued

Urinary analysis in $F_2$ generation of transgenic rat
Line; R12121-7 derived $F_2$ generation (heterozygote and homozygote)

| Individual No. | Sex | 11w | 14w | 17w | 21w | 24w | 27w | 30w |
|---|---|---|---|---|---|---|---|---|
| Homozygote | | | | | | | | |
| 7-1 | ♂ | 2.99 | 2.86 | 5.44 | 8.77 | 18.2 | 28.0 | — |
| 7-3 | ♀ | 0.61 | 0.87 | 0.80 | 1.61 | 1.05 | 1.79 | 1.35 |
| 7-5 | ♀ | 1.01 | 0.94 | 1.22 | 0.82 | 0.78 | 1.16 | 1.17 |
| 7-11 | ♀ | 1.25 | 1.06 | 0.46 | 0.59 | 0.92 | 2.15 | 1.38 |
| 7-12 | ♂ | 9.15 | 8.36 | 11.4 | 17.0 | 24.7 | 25.4 | 28.2 |
| Control | | | | | | | | |
| 1 | ♂ | 1.05 | 0.72 | 1.76 | 0.44 | 1.97 | 1.45 | |
| 2 | ♂ | 0.96 | 1.02 | 0.82 | 0.69 | 1.32 | 1.26 | |
| 3 | ♂ | 0.95 | 0.31 | 0.55 | 0.54 | 0.82 | 0.76 | |
| 4 | ♂ | 0.63 | 0.65 | 1.46 | 0.86 | 1.10 | 0.43 | |
| 5 | ♂ | 0.93 | 0.75 | 1.35 | 0.76 | 2.15 | 0.75 | |
| Mean ± S.D. | | 0.90 ± 0.16 | 0.69 ± 0.25 | 1.19 ± 0.49 | 0.66 ± 0.17 | 1.47 ± 0.6 | 0.93 ± 0.4 | |
| Control | | | | | | | | |
| 1 | ♀ | 0.54 | 1.31 | 0.65 | 0.82 | 1.62 | 0.53 | |
| 2 | ♀ | 1.05 | 0.66 | 2.06 | 1.07 | 0.53 | 1.49 | |
| 3 | ♀ | 0.89 | 0.89 | 0.45 | 0.70 | 1.97 | 0.54 | |
| 4 | ♀ | 0.79 | 0.71 | 1.24 | 0.47 | 1.95 | 1.54 | |
| 5 | ♀ | 0.95 | 0.65 | 1.08 | 0.72 | 1.80 | 1.80 | |
| Mean ± S.D. | | 0.84 ± 0.19 | 0.84 ± 0.28 | 1.10 ± 0.63 | 0.76 ± 0.22 | 1.75 ± 0.8 | 1.10 ± 0.5 | |

6) Blood biochemistry of rats into which the 25-hydroxyvitamin $D_3$ 24-hydroxylase gene is introduced For determining the blood biochemical markers, the blood was withdrawn from each transgenic rat in the routine manner. The assay of blood total cholesterol (TCHO) was carried out colorimetrically using a commercial kit (Fuji Fiol Co.). Blood total triglyceride (TG) was also determined colorimetrically using a commercial kit (Fuji Film Co.). Blood total glucose (GLU) was determined colorimetrically using a commercial kit (Fuji Film Co.). Blood calcium (Ca) was determined colorimetrically using the commercial kit Calcium E-Test Wako (Wako Pure Chemical Ind.). Blood phosphorus (P) was determined colorimetrically using the commercial kit Phospholipid C-Test Wako (Wako Pure Chemical Ind.). Blood creatinine (CREA) was determined colorimetrically using a commercial kit (Fuji Film Co.). In addition, creatinine clearance (ml/min/100 g body weight) (Ccr) was calculated from measured blood creatinine and urinary creatinine values for each individual by means of the equation; urinary creatinine value×24-hr urine volume/blood creatinine value/body weight×100/1440.

Referring to blood total cholesterol in $F_0$ transgenic rats, R12123-6 (female) showed the highest value over 200 mg/dl. The values in the other transgenic rats were 60 to 150 mg/dl. The highest blood triglyceride level of 2265 mg/dl was registered in R12123-6, and R11293-5 and R02205-1 also showed high values. The blood glucose level was not varying much among the transgenic rats. The blood calcium level was not varying much, either, among the transgenic rats. The blood phosphorus level was as high as 752 mg/dl in R12123-6. The creatinine clearance value in R09121-7 was as low as less than 0.2 ml/min/100 g body weight.

The blood total cholesterol level was highest in R12121-7-4 (female) among transgenic rats of $F_1$ generation, being 228 mg/dl. The levels in the other transgenic rats were 64 to 120 mg/ml. The blood triglyceride level was as high as 331 mg/dl in R12121-7-4. The blood glucose level did not very appreciably among the transgenic rats. The blood calcium level was not varying much, either, among the transgenic rats. In blood phosphorus, R12121-7-4 gave the highest value of 375 mg/dl. Creatinine clearance did not vary much among the animals investigated (Table 8).

TABLE 8

Blood analysis in $F_1$ and $F_2$ generations of transgenic rat expressing MLV-LTR-Vitamin $D_3$ 24-hydroxylase

| | Serum | | | | | | |
|---|---|---|---|---|---|---|---|
| Line No. | TCHO (mg/dl) | TG (mg/dl) | GLU (mg/dl) | Ca (mg/dl) | P (mg/dl) | CREA (mg/dl) | Ccr (ml/min/100 g.bwt) |
| F0 | | | | | | | |
| R09121-7 | 124 | 107 | 116 | 9.4 | 165 | 0.7 | 0.173 |
| R10175-9 | 150 | 286 | 136 | 9.7 | 272 | 0.6 | 0.411 |
| R11293-5 | 82 | 640 | 108 | 9.3 | 258 | 0.6 | 0.282 |
| R12121-7 | 78 | 271 | 114 | 8.9 | 214 | 0.6 | 0.261 |

TABLE 8-continued

Blood analysis in $F_1$ and $F_2$ generations of transgenic rat expressing MLV-LTR-Vitamin $D_3$ 24-hydroxylase

| Line No. | Serum | | | | | | |
|---|---|---|---|---|---|---|---|
| | TCHO (mg/dl) | TG (mg/dl) | GLU (mg/dl) | Ca (mg/dl) | P (mg/dl) | CREA (mg/dl) | Ccr (ml/min/100 g.bwt) |
| R12123-6 | 233 | 2265 | 114 | 8.9 | 752 | 0.6 | 0.-254 |
| R01163-1 | 60 | 191 | 120 | 10.0 | 164 | 0.7 | 0.231 |
| R02205-1 | 68 | 394 | 111 | 9.5 | 214 | 0.7 | 0.234 |
| F1 | | | | | | | |
| R12121-7-4 | 228 | 331 | 117 | 9.7 | 375 | 1.2 | |
| R12123-6-3 | 120 | 183 | 158 | 10.0 | 221 | 0.5 | 0.292 |
| R12123-6-5 | 64 | 200 | 146 | 9.6 | 189 | 0.7 | 0.294 |
| R12123-6-9 | 90 | 205 | 123 | 9.5 | 210 | 0.6 | 0.243 |

In regard of blood total cholesterol, whereas the mean value of male control rats was 71 mg/dl and the mean of female control rats was 84 mg/dl, high values around 200 mg/dl were found in R12121-7-12 and -13 among the male transgenic rats of $F_2$ generation at week 24. With regard to blood triglyceride, whereas the mean of male control rats was 95.6 mg/dl and that of female control rats was 144 mg/dl, R12121-7-12 and -13 showed values over 400 mg/dl. As to blood glucose, whereas the mean values of male control rats and female control rats were 122 mg/dl and 124 mg/dl, respectively, the blood glucose levels in the transgenic rats were 86 to 131 mg/dl, thus showing no remarkable difference from the control values. Regarding blood calcium, whereas the mean value of male control rats was 9.2 mg/dl and that of female control rats was 9.7 mg/dl, the concentrations in the transgenic rats were 8.8 to 10.1 mg/dl, thus showing no remarkable differences from the control values. In regard of blood phosphorus, whereas the mean values of male control rats and female control rats were 126 mg/dl and 174 mg/dl, respectively, the levels in R12121-7-12 and -13 were as high as more than 300 mg/dl. As to creatinine clearance, whereas the mean value of male control rats was 0.376 ml/min/100 g body weight and that of female control rats was 0.366 ml/min/100 g body weight, R12121-7-4, -10, -1, -11, -12 and -13 gave values less than 0.3 (Table 9).

TABLE 9

Blood analysis in transgenic rat expressing MLV-LTR-Vitamin $D_3$ 24-hydroxylase
Line; R12121-7 derived $F_2$ first offspring (at 24 weeks old)

| Individual No. | Serum | | | | | | |
|---|---|---|---|---|---|---|---|
| | TCHO (mg/dl) | TG (mg/dl) | GLU (mg/dl) | Ca (mg/dl) | P (mg/dl) | CREA (mg/dl) | Ccr (ml/min/100 g.bwt) |
| Heterozygote | | | | | | | |
| 7-4 | 69 | 221 | 124 | 9.1 | 211 | 0.7 | 0.252 |
| 7-7 | 79 | 189 | 111 | 10.1 | 203 | 0.5 | 0.382 |
| 7-8 | 81 | 175 | 114 | 8.8 | 187 | 0.6 | 0.356 |
| 7-10 | 88 | 105 | 119 | 8.9 | 185 | 0.6 | 0.212 |
| 7-13 | 201 | 400 | 100 | 9.4 | 316 | 0.7 | 0.208 |
| 7-15 | 95 | 248 | 115 | 9.4 | 160 | 0.6 | 0.308 |
| Homozygote | | | | | | | |
| 7-1 | 147 | 183 | 131 | 9.4 | 249 | 0.6 | 0.277 |
| 7-3 | 72 | 371 | 122 | 9.5 | 222 | 0.6 | 0.354 |
| 7-5 | 73 | 390 | 86 | 9.5 | 230 | 0.5 | 0.360 |
| 7-11 | 56 | 162 | 129 | 9.2 | 136 | 0.8 | 0.212 |
| 7-12 | 198 | 439 | 92 | 9.7 | 364 | 0.7 | 0.282 |
| Control | | | | | | | |
| 1(♂) | 82 | 98 | 114 | 9.4 | 158 | 0.7 | 0.330 |
| 2 | 89 | 108 | 120 | 9.7 | 132 | 0.5 | 0.418 |
| 3 | 63 | 98 | 134 | 9.3 | 115 | 0.6 | 0.423 |
| 4 | 59 | 86 | 121 | 8.9 | 115 | 0.7 | 0.328 |
| 5 | 61 | 88 | 122 | 8.9 | 110 | 0.7 | 0.383 |
| Mean ± S.D | 71 ± 13.7 | 95.6 ± 8.9 | 122 ± 7.3 | 9.2 ± 0.3 | 126 ± 20 | 0.64 ± 0.09 | 0.376 ± 0.05 |
| 6(♀) | 82 | 198 | 105 | 10.0 | 172 | 0.8 | 0.412 |
| 7 | 71 | 110 | 118 | 9.6 | 206 | 0.8 | 0.358 |
| 8 | 90 | 169 | 1.38 | 9.5 | 165 | 0.6 | 0.364 |
| 9 | 73 | 94 | 125 | 9.5 | 164 | 0.9 | 0.386 |
| 10 | 104 | 151 | 136 | 10.0 | 162 | 0.7 | 0.308 |
| Mean ± S.D | 84 ± 13.5 | 144 ± 42.6 | 124 ± 13.6 | 9.7 ± 0.3 | 174 ± 18 | 0.76 ± 0.11 | 0.366 ± 0.04 |

The biochemical markers in the same animals at week 27 after birth were as follows. As to blood total cholesterol, whereas the mean values of male and female control rats were 62.4 mg/dl and 70.6 mg/dl, respectively, R12121-7-12 and -13 gave high values in excess of 200 mg/dl. With regard to blood triglyceride, whereas the mean values of male and female control rats were 113 mg/dl and 166 mg/dl, respectively, R12121-7-7, -1, -3, -12 and -13 gave values in excess of 300 mg/dl. There was no remarkable variation in blood glucose concentration; whereas the mean values of male control rats and female control rats were 149 mg/dl and 117 mg/dl, respectively, the concentration values in the transgenic rats were 113 to 156 mg/dl. As to blood calcium, whereas the mean concentration values of male and female control rats were 9.1 mg/dl and 9.5 mg/dl, respectively, the concentration values in the transgenic rats were 8.2 to 10.2 mg/dl, thus showing no remarkable difference from the control. As to blood phosphorus, whereas the mean values of male control rats and female control rats were 129 mg/dl and 172 mg/dl, respectively, R12121-7-1, -12 and -13 showed high values over 300 mg/dl. In regard of creatinine clearance, whereas the mean values of male control rats and female control rats were 0.365 ml/min/100 g body weight and 0.442 ml/min/100 g body weight, respectively, R12121-7-10, -1, -7, -15, -11, -5 and -12 gave values less than 0.3. Thus, the values of various markers varied from week to week in the same animal but abnormal values were generally found in the same animals (Table 10).

femoral bones were isolated from each carcass in the routine manner. Those organs and tissues were respectively fixed in 10% formalin, embedded in paraffin, sectioned with a microtome, and stained with hematoxylin-eosin in the routine manner to provide specimens. The femoral bone was dished with 10% formic acid for 3 days in the routine manner, sectioned sagittally and treated in the same manner as the other organs to provide specimens. The specimens were examined under the light microscope.

As a result, the cerebrum was unchanged in R12121-7-1 and control rats. The cerebellum was also unchanged in R12121-7-1 and control rats. In control rats, the liver showed cellular infiltration of Glisson's capsule. In R12121-7-1, cellular infiltration of Glisson's capsule, vacuolation of liver cells and disseminated clear cells were observed. The kidney was unchanged in control rats. In contrast, R12121-7-1 showed glomeruloscrelosis, nephropathy, simple hyperplasia of ureter, basophilic degeneration of renal tubular epithelium, hyaline casts, dilatation of renal tubules and small round cell infiltration. The lung was unchanged in control rats. In R12121-7-1, thickening of the tunicae media and externa of the small and medium arteries of the lung, alveolar histiocytosis, ossification, calcification of pulmonary arteries, and localized thickening of alveolar septa were observed. The heart was unchanged in R12121-7-1 and control rats. In control rats, the spleen showed extramedullary hemopoiesis and pigmentation. In R12121-7-1, extramedullary hemopoiesis and arterial hypertrophy were

TABLE 10

Blood analysis in transgenic rat expressing MLV-LTR-Vitamin $D_3$ 24-hydroxylase Line; R12121-7 derived $F_2$ first offspring (at 27 weeks old)

| Individual No. | Serum | | | | | | |
|---|---|---|---|---|---|---|---|
| | TCHO (mg/dl) | TG (mg/dl) | GLU (mg/dl) | Ca (mg/dl) | P (mg/dl) | CREA (mg/dl) | Ccr (ml/min/100 g.bwt) |
| Heterozygote | | | | | | | |
| 7-4 | 80 | 182 | 129 | 9.5 | 191 | 0.6 | 0.315 |
| 7-7 | 74 | 300 | 133 | 10.0 | 218 | 0.7 | 0.254 |
| 7-8 | 78 | 139 | 156 | 9.2 | 164 | 0.6 | 0.358 |
| 7-10 | 86 | 57 | 118 | 8.2 | 161 | 1.2 | 0.154 |
| 7-13 | 206 | 341 | 113 | 9.2 | 331 | 0.7 | 0.362 |
| 7-15 | 87 | 268 | 128 | 9.6 | 217 | 0.6 | 0.259 |
| Homozygote | | | | | | | |
| 7-1 | 184 | 312 | 136 | 10.0 | 327 | 0.6 | 0.264 |
| 7-3 | 75 | 369 | 136 | 9.9 | 226 | 0.6 | 0.326 |
| 7-5 | 87 | 211 | 133 | 9.4 | 203 | 0.7 | 0.256 |
| 7-11 | 63 | 63 | 134 | 8.6 | 136 | 1.4 | 0.135 |
| 7-12 | 233 | 498 | 118 | 10.2 | 402 | 0.8 | 0.295 |
| Control | | | | | | | |
| 1(♂) | 73 | 144 | 138 | 9.4 | 156 | 0.6 | 0.317 |
| 2 | 79 | 130 | 157 | 9.7 | 146 | 0.5 | 0.310 |
| 3 | 58 | 117 | 150 | 9.2 | 124 | 0.6 | 0.384 |
| 4 | 50 | 89 | 149 | 8.8 | 108 | 0.7 | 0.404 |
| 5 | 52 | 87 | 149 | 8.6 | 111 | 0.7 | 0.410 |
| Mean ± S.D | 62.4 ± 12.9 | 113 ± 2.5 | 149 ± 6.8 | 9.1 ± 0.3 | 129 ± 21.3 | 0.62 ± 0.09 | 0.365 ± 0.05 |
| 6(♀) | 78 | 112 | 117 | 8.7 | 180 | 0.8 | 0.392 |
| 7 | 52 | 212 | 109 | 9.4 | 161 | 0.8 | 0.505 |
| 8 | 84 | 178 | 129 | 10.1 | 168 | 0.6 | 0.520 |
| 9 | 62 | 164 | 102 | 9.7 | 154 | 0.7 | 0.368 |
| 10 | 77 | 164 | 127 | 9.7 | 195 | 0.8 | 0.424 |
| Mean ± S.D | 70.6 ± 13.2 | 166 ± 36 | 117 ± 11.5 | 9.5 ± 0.5 | 172 ± 16.2 | 0.74 ± 0.1 | 0.442 ± 0.07 |

7) Histopathological analysis of rats into which the 25-hydroxyvitamin $D_3$ 24-hydroxylase gene introduced R12121-7-1 (homozygote, male, 28 weeks old), a transgenic rat of $F_2$ generation, and control rats were sacrificed and the brain, heart, liver, lungs, kidneys, spleen, testes and observed. The bone marrow was unchanged in control rats. In contrast, R12121-7-1 showed increased hemopoiesis. The testis was unchanged in R12121-7-1 and control rats.

8) Organ weights of the 25-hydroxyvitamin $D_3$ 24-hydroxylase gene transgenic rats The transgenic rat $F_4$ R12121-7-1 (homozygote, male, 18 weeks old) and control rats were sacrificed and the heart, liver, lung, kidney and spleen were isolated from each carcass in the routine manner and weighed. As a result, the heart, liver, lung and spleen weights were significantly greater than the corresponding organ weights of control rats. The kidney weight tended to be greater in comparison with control rats.

9) Bone-mineral densities of the foreign 25-hydroxyvitamin $D_3$ 24-hydroxylase gene transgenic rats The $F_3$ progeny of the transgenic rat R12121-7-1 (homozygote, 16 weeks old) and control rats were sacrificed and the femoral bones and tibiae were isolated from each carcass. The bone-salt density of each bone was measured by double energy X-ray absorptiometry (generally abbreviated as DXA). As a result, the bone-salt density of the $\frac{1}{3}$ proximal epiphysial portion of tibia of the male and female transgenic rats was significantly low as compared with control rats of respective genders. In addition, the bone-mineral density of the $\frac{1}{3}$ distal epiphysial portion of femoral bones of the male transgenic rats tended to be lower than that of the control rats.

10) Gene expression analysis of the 25-hydroxyvitamin $D_3$ 24-hydroxylase gene transgenic rats The RNA for analysis was harvested from portions of the brain, heart, liver, lung, kidney, spleen, testis and femoral bone from each of said transgenic $F_2$ rat R12121-7-1 (homozygote, 28 weeks old) and control rats by tissue disruption in guanidine and subsequent extraction according to the routine procedure. Each nucleic acid pellet obtained was washed in 70% ethanol, dried and resuspended in sterile water.

Figure 9:
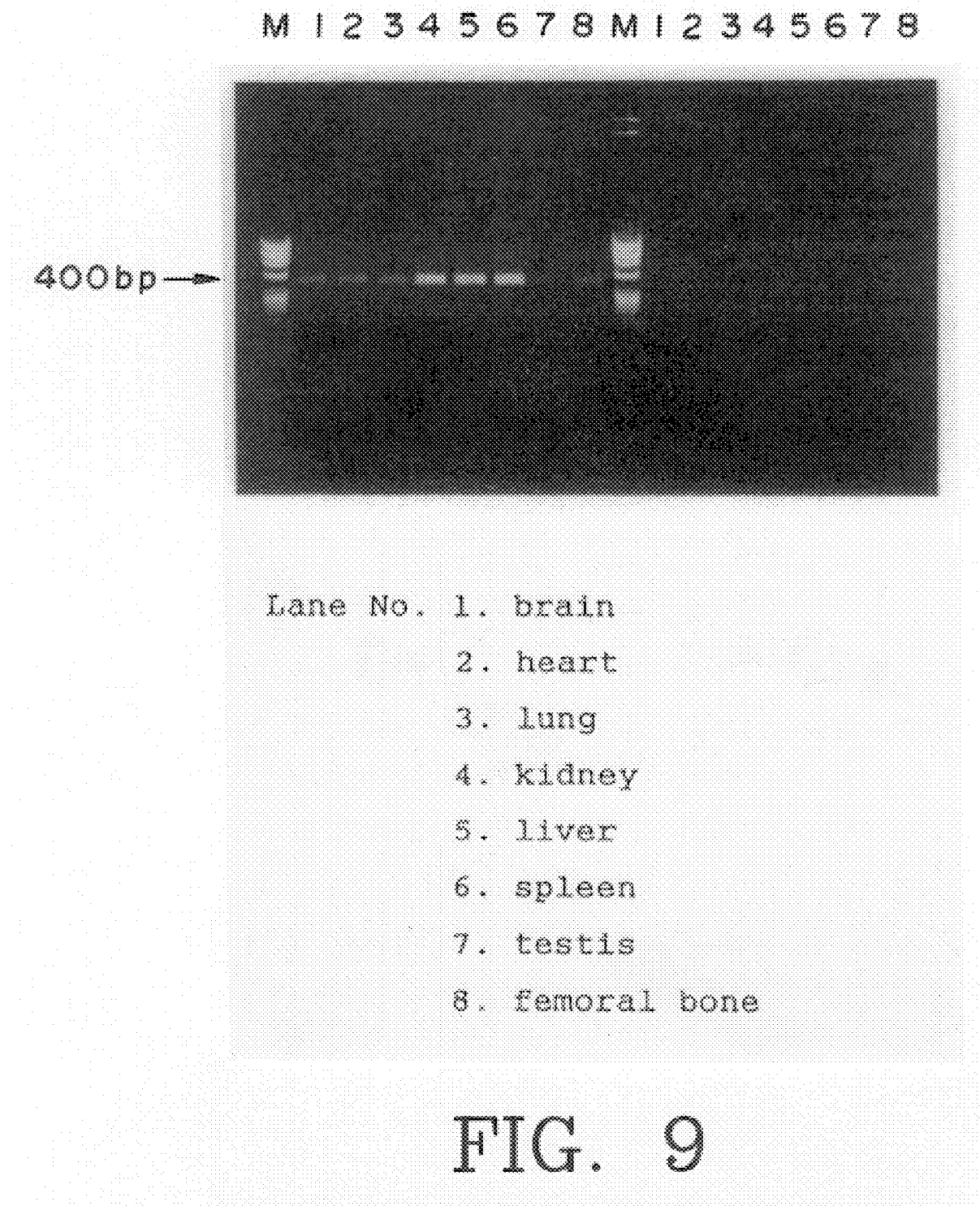
FIG. 9 shows the result of a gene expression analysis (RT-PCR; electrophoresis) of the transgenic rat $F_2$ offspring, R12121-7-1.

The reverse transcriptase polymerase chain reaction (generally abbreviated as RT-PCR) was carried out using the primers 5 and 6 described hereinbefore. Using 20 μg of the RNA preparation as substrate, it was first treated with reverse transcriptase at 60° C. for 30 minutes and further at 94° C. for 2 minutes. Then, Taq polymerase was added and the reaction cycle at 94° C. for 1 min. and at 60° C. for 1.5 min. was repeated in 40 times, followed by incubation at 60° C. for 7 minutes. The reaction mixture was electrophoresed in 1.0% agarose GTG (FMC Bio-Products) gel. In the case of control rats, no DNA band was observed for any of the organs analyzed. In contrast, all the organs from R12121-7-1 gave a 400 bp DNA band (FIG. 9).

Expression of the 25-hydroxyvitamin $D_3$ 24-hydroxylase gene was found in the brain, heart, liver, lung, kidney, spleen, testis and femoral bone of the transgenic $F_2$ rat R12121-7-1 (homozygote, male, aged 28weeks). In controls, the expression of the intrinsic 25-hydroxyvitamin $D_3$ 24-hydroxylase gene was also below the detection. limit.

Industrial Applicability

The nonhuman mammal into which a foreign 25-hydroxyvitamin $D_3$ 24-hydroxylase gene is introduced, of this invention can be expected to have hypercalcemia, hypocalcemia, hyperparathyroidism, bone disease, such as rickets, osteomalacia, osteoporosis and loss of bone mass, renal disease such as glomerulonephritis, glomeruloscrelosis, chronic nephritis and renal insufficiency, even joint disease, pulmonary disease, hyperlipidemia, arteriosclerosis, cardiac disease, diabetes, obesity, digestive organ disease, infectious disease, allergic disease, endocrine disease, dementia and/or cancer or complications thereof and can therefore be used as an animal model for such diseases. For example, the rat of this invention can be used for the unraveling of the mechanisms of said diseases, explorations for the development of prophylactic and therapeutic modalities for the diseases, and the screening of candidate therapeutic drugs.

The transgenic animal of this invention can be used as a disease model for the tracking of the disease state in bone disorders such as osteoporosis, osteomalacia, etc., disorders of the kidney such as nephritis, renal insufficiency, etc., as a model for the therapy of said and other diseases arising from abnormalities of vitamin $D_3$ metabolism, as a model for the screening of candidate compounds for the development of new drugs, and as a source of cells suitable for the in vitro evaluation thereof.

This invention has shed light on the mechanism of onset of renal disease, bone disease, joint disease, pulmonary disease, hyperlipidemia, arteriosclerosis, cardiac disease, diabetes, obesity, digestive organ disease, infectious disease, allergic disease, endocrine disease, dementia or cancer, or a complication of such disease, through the excess expression of 25-hydroxyvitamin $D_3$ 24-hydroxylase which promotes an imbalance of vitamin $D_3$ metabolism chiefly in the kidneys and an inactivation or suppression of the gene which regulates the active forms of vitamin $D_3$. In particular, it has been elucidated that renal insufficiency is caused by abnormalities of vitamin $D_3$ metabolism, particularly an excess expression of vitamin $D_3$ 24-hydroxylase. This is a new finding.

The nonhuman mammal into which a foreign 25-hydroxyvitamin $D_3$ 24-hydroxylase gene is introduced, of this invention can be utilized for the supply of 25-hydroxyvitamin $D_3$ 24-hydroxylase gene high-expression cells and the unraveling of the target gene regulatory mechanism of nuclear receptors.

What is claimed is:

1. A rat comprising a rat 25 hydroxyvitamin $D_3$ 24-hydroxylase transgene which over-expresses said 25 hydroxyvitamin $D_3$ 24-hydroxylase transgene and exhibits a phenotype, resulting from said over-expression, selected from the group consisting of:

(1) increased blood total cholesterol level, (2) increased blood triglyceride level, (3) increased urinary albumin concentration, (4) lower bone-salt density, (5) lower bone-mineral density (6) glomerulosclerosis, (7) nephropathy, (8) simple hyperplasia of the renal ureter, (9) basophilic degeneration of renal tubular epithelium,

(10) hyaline casts in the kidney,

(11) dilatation of renal tubules,

(12) small round cell infiltration in the kidney,

(13) thickening of the tunicae media and externa of the small and medium arteries of the lung,

(14) alveolar histicytosis,

(15) ossification in the lung,

(16) calcification of pulmonary arteries in the lung,

(17) localized thickening of alveolar septa in the lung,

(18) hemopoiesis, and

(19) arterial hypertrophy in the spleen.

2. The rat according to claim 1, wherein the phenotype is increased blood total cholesterol level or increased blood triglyceride level.

3. A method of screening for a substance to be used for preventing and/or treating an endocrine disease, which comprises administering an investigational substance to the rat according to claim 1 and assaying efficacy of said investigational substance in said endocrine disease.

4. A method of constructing the rat according to claim 1 which comprises introducing a DNA, into which a rat 25-hydroxyvitamin $D_3$ 24-hydroxylase gene is inserted, into a fertilized egg harvested by mating a female rat injected with about 20 to 50 IU/animal of follicle stimulating hormone and then with about 0 to 10 IU/animal of luteinizing hormone with a male rat at approximately 48 hours after pretreatment of follicle stimulating hormone and implanting said fertilized egg in a female rat.

5. A method of constructing the rat according to claim 1 which comprises implanting a fertilized egg incorporating a DNA into which a rat 25-hydroxyvitamin $D_3$ 24-hydroxylase gene is inserted, in a pseudopregnant female rat which is given luteinizing hormone-releasing hormone or an analog thereof and then mated with a male rat at approximately 4 days after injection of luteinizing hormone-releasing hormone or an analog thereof.

6. A cell isolated from the transgenic rat of claim 1, wherein said cell comprises a transgene comprising a DNA sequence encoding 25 hydroxyvitamin $D_3$ 24-hydroxylase.

7. An isolated cell of claim 6, wherein the cell is a kidney cell and wherein the transgene is over-expressed in kidneys at detectable levels.

8. An isolated cell of claim 6, wherein the cell is from bone tissue and wherein the transgene is over-expressed in bone tissue at detectable levels.

9. An isolated cell of claim 6, wherein the cell is a liver cell and wherein the transgene is over-expressed in the liver at detectable levels.

10. An isolated cell of claim 6, wherein the cell is a lung cell and wherein the transgene is over-expressed in lung tissue at detectable levels.

11. A rat comprising a rat 25-hydroxyvitamin $D_3$ 24-hydroxylase transgene, wherein the rat is characterized by over-expression of 25-hydroxyvitamin $D_3$ 24-hydroxylase, and the promotion of an imbalance of vitamin $D_3$ metabolism chiefly in the kidneys and the inactivation or suppression of the activated vitamin $D_3$-regulating genes.

12. The rat of claim 11, wherein the rat is characterized by having loss of bone mass, low bone-salt and bone-mineral densities, increased hemopoiesis or greater organ weights.

13. The rat of claim 11, wherein the rat is characterized by glomeruloscrelosis, nephropathy, simple hyperplasia of renal ureter, basophilic degeneration of renal tubular epithelium, hyaline casts in the kidney, dilatation of renal tubules, increased urinary albumin concentration, or small round cell infiltration of the kidney.

14. The rat of claim 11, wherein the rat is characterized by cellular infiltration of Glisson's capsule, vacuolation of liver cells or disseminated clear cells.

15. The rat of claim 11, wherein the rat is characterized by thickening of the tunicae media and externa of the small and medium arteries of the lung, alveolar histiocytosis, ossification in the lung, calcification of pulmonary arteries, or localized thickening of alveolar septa.

16. A method of screening for a substance to be used for preventing and/or treating an endocrine disease, which comprises administering an investigational substance to the rat according to claim 11 and assaying efficacy of said investigational substance in said endocrine disease.

* * * * *